United States Patent
Nishio et al.

(10) Patent No.: US 10,653,441 B2
(45) Date of Patent: May 19, 2020

(54) ATHERECTOMY WITH SUBINTIMAL SPACE

(71) Applicant: TERUMO KABUSHIKI KAISHA, Shibuya-ku, Tokyo (JP)

(72) Inventors: Kousuke Nishio, Machida (JP); Yuuichi Tada, Tokyo (JP)

(73) Assignee: TERUMO KABUSHIKI KAISHA, Shibuya-Ku, Tokyo (JP)

( * ) Notice: Subject to any disclaimer, the term of this patent is extended or adjusted under 35 U.S.C. 154(b) by 493 days.

(21) Appl. No.: 15/453,427

(22) Filed: Mar. 8, 2017

(65) Prior Publication Data

US 2018/0256196 A1    Sep. 13, 2018

(51) Int. Cl.
*A61B 17/3207*    (2006.01)
*A61B 17/22*    (2006.01)

(52) U.S. Cl.
CPC .. *A61B 17/320758* (2013.01); *A61B 17/3207* (2013.01); *A61B 17/320725* (2013.01); *A61B 2017/22039* (2013.01); *A61B 2017/22069* (2013.01); *A61B 2017/320733* (2013.01); *A61B 2017/320741* (2013.01)

(58) Field of Classification Search
CPC .... A61B 17/320708; A61B 17/320725; A61B 2017/320741; A61B 17/32075
See application file for complete search history.

(56) References Cited

U.S. PATENT DOCUMENTS

| | | | | |
|---|---|---|---|---|
| 4,290,427 A * | 9/1981 | Chin | A61B 17/320016 | 606/159 |
| 4,315,511 A * | 2/1982 | Chin | A61B 17/32075 | 15/104.16 |
| 4,621,636 A * | 11/1986 | Fogarty | A61B 17/32075 | 606/159 |
| 5,415,656 A * | 5/1995 | Tihon | A61B 18/14 | 606/46 |
| 5,820,629 A * | 10/1998 | Cox | A61B 17/3207 | 606/159 |
| 5,843,102 A * | 12/1998 | Kalmann | A61B 17/3201 | 606/159 |
| 6,241,745 B1 * | 6/2001 | Rosenthal | A61B 17/00008 | 606/159 |
| 6,331,166 B1 * | 12/2001 | Burbank | A61B 10/0266 | 600/567 |
| 6,540,695 B1 * | 4/2003 | Burbank | A61B 10/0266 | 600/564 |
| 6,659,105 B2 * | 12/2003 | Burbank | A61B 10/0266 | 128/898 |

(Continued)

*Primary Examiner* — Wade Miles
(74) *Attorney, Agent, or Firm* — Buchanan Ingersoll & Rooney PC

(57) ABSTRACT

A method and dissecting device are disclosed for treating a stenotic vessel. The method including inserting a first dissecting member into a subintimal space of a blood vessel and a second dissecting device configured to be received within a lumen within the first dissecting device and inserted into the blood vessel in a bent state; dissecting an inner side of the subintimal space from an outer side of the subintimal space over an entire circumference of the blood vessel with the first dissecting device; and removing the dissected inner side of the subintimal space and a stenotic region attached to the inner side of the subintimal space from the blood vessel.

10 Claims, 41 Drawing Sheets

(56) References Cited

U.S. PATENT DOCUMENTS

| | | | |
|---|---|---|---|
| 7,044,956 B2* | 5/2006 | Vetter | A61B 10/0266 606/167 |
| 10,159,509 B2* | 12/2018 | Nishio | A61B 17/32070 |
| 2002/0029052 A1* | 3/2002 | Evans | A61B 17/22 606/159 |
| 2004/0193204 A1* | 9/2004 | Lafontaine | A61B 17/22 606/190 |
| 2006/0235366 A1* | 10/2006 | Simpson | A61B 17/32078 604/508 |
| 2007/0093779 A1* | 4/2007 | Kugler | A61B 17/221 604/509 |
| 2007/0093780 A1* | 4/2007 | Kugler | A61B 17/221 604/510 |
| 2008/0154293 A1* | 6/2008 | Taylor | A61B 17/32053 606/170 |
| 2008/0228171 A1* | 9/2008 | Kugler | A61B 17/221 604/529 |
| 2009/0138031 A1* | 5/2009 | Tsukernik | A61B 17/32075 606/159 |
| 2011/0264133 A1* | 10/2011 | Hanlon | A61M 25/007 606/194 |
| 2012/0197277 A1* | 8/2012 | Stinis | A61B 17/221 606/159 |
| 2014/0222044 A1* | 8/2014 | Ladd | A61B 17/320758 606/159 |
| 2014/0222047 A1* | 8/2014 | Vreeman | A61B 17/3207 606/159 |
| 2015/0119910 A1 | 4/2015 | Alvarez et al. | |
| 2016/0045714 A1 | 2/2016 | Zhou | |
| 2018/0055535 A1* | 3/2018 | Tada | A61B 17/320725 |

* cited by examiner

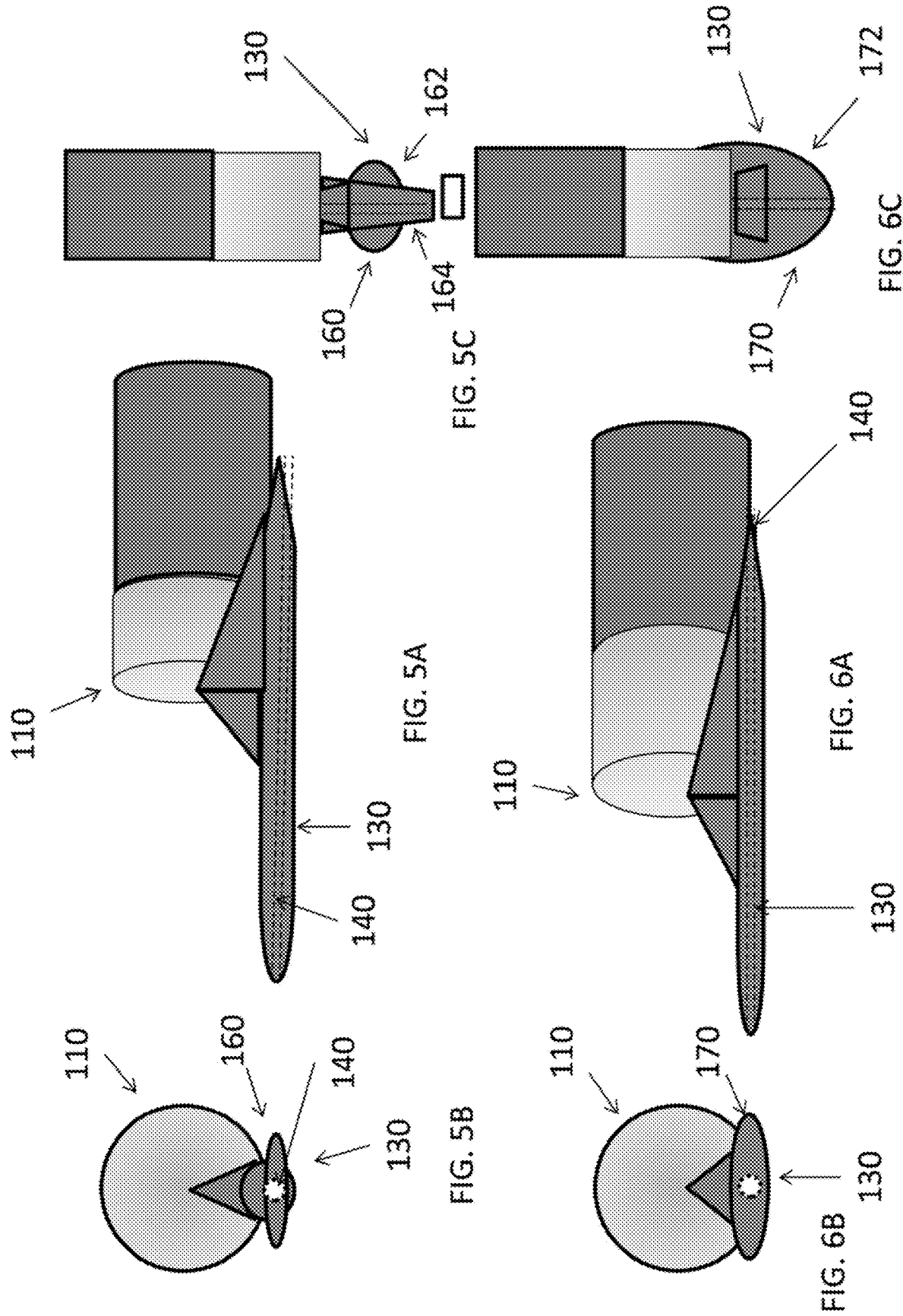

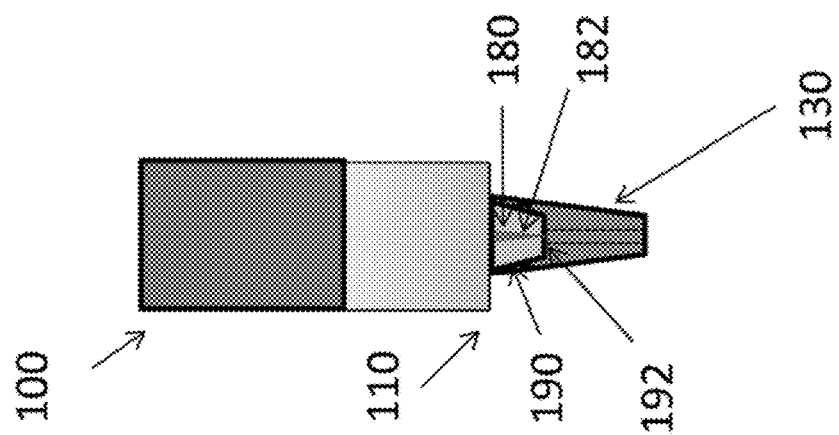
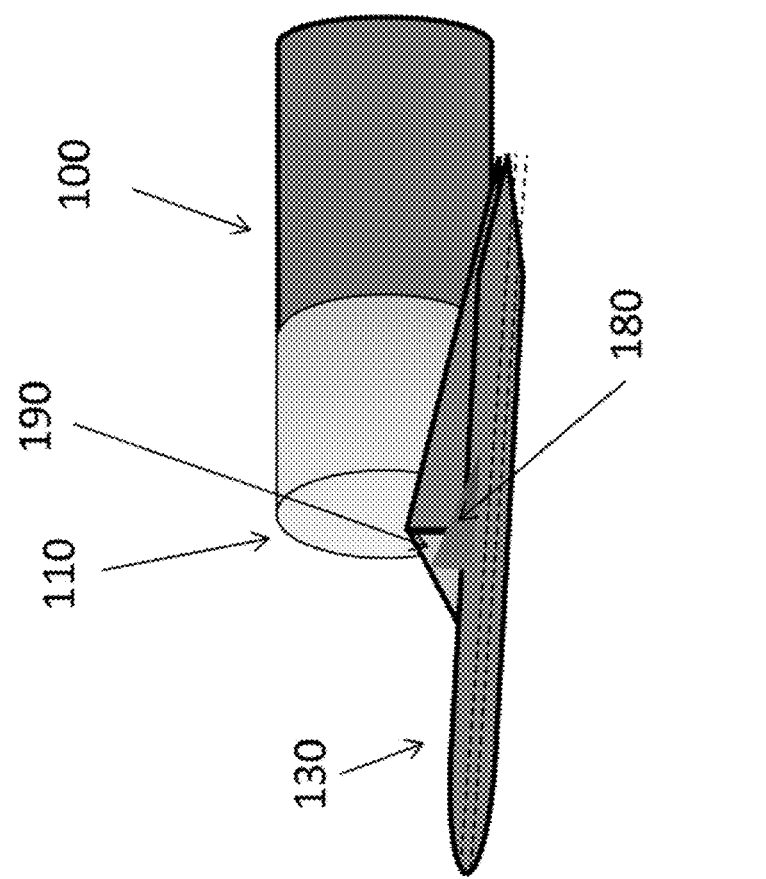
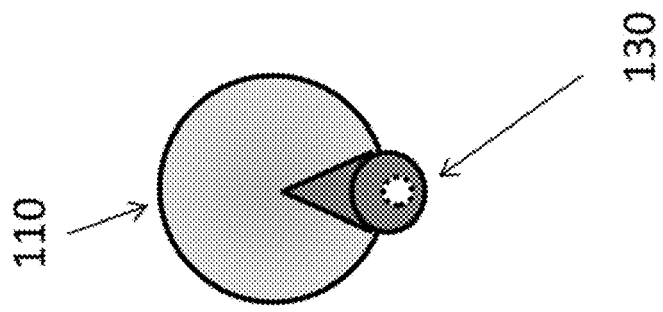

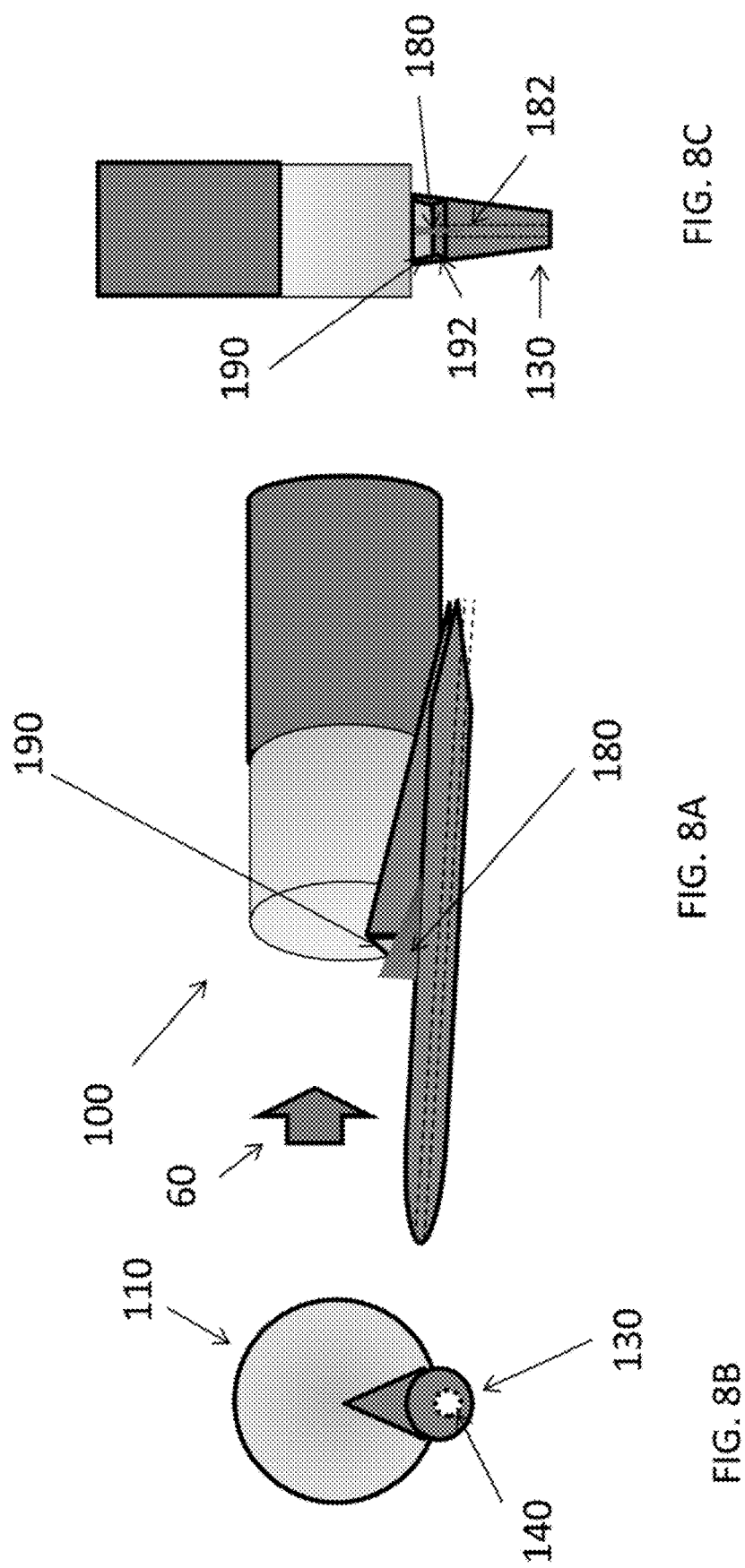

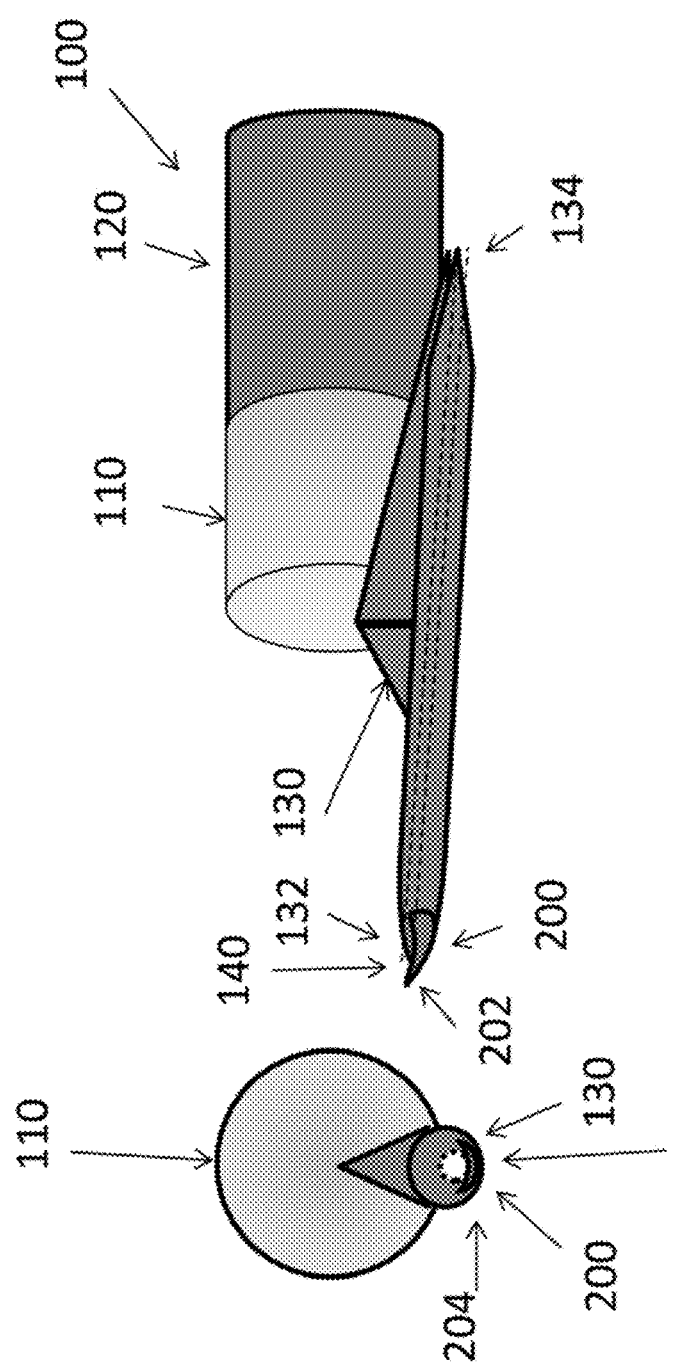

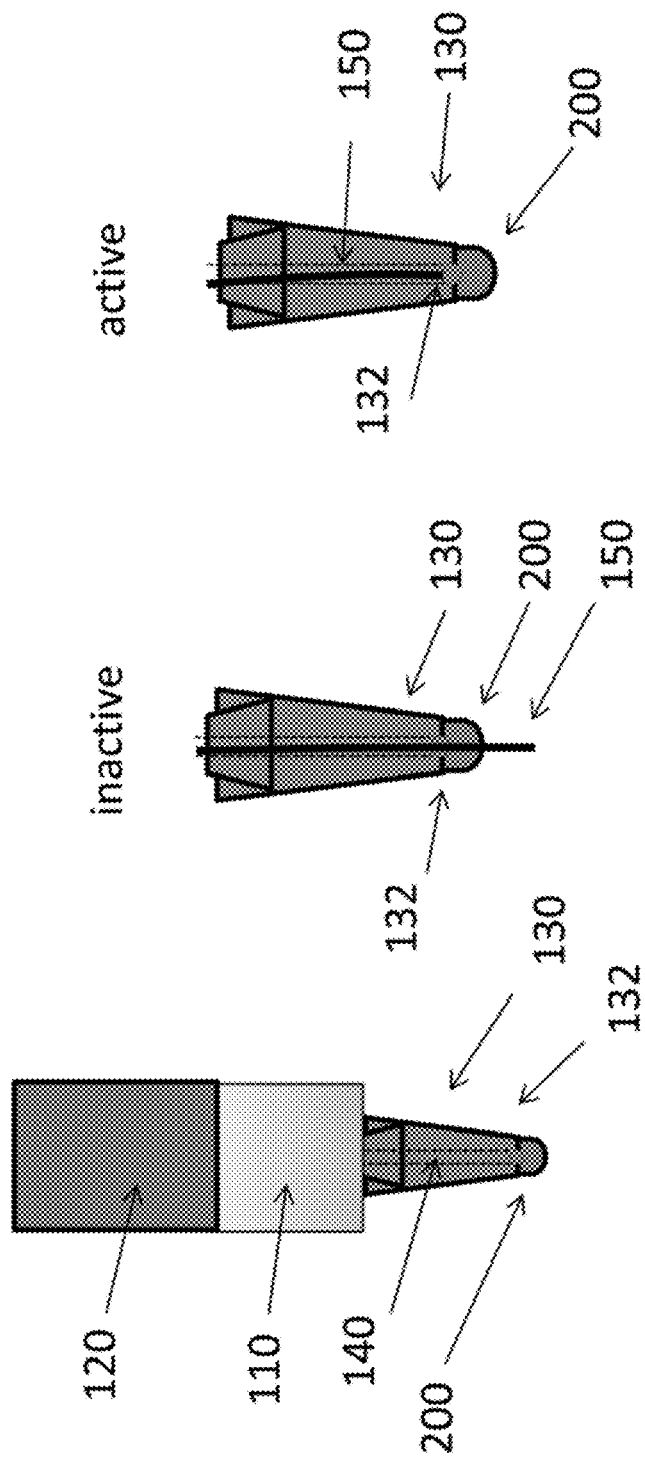

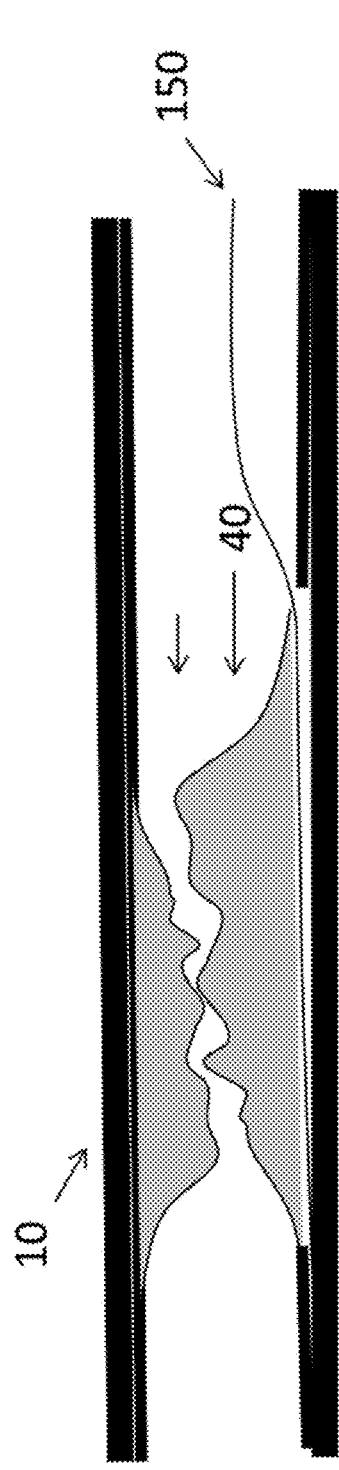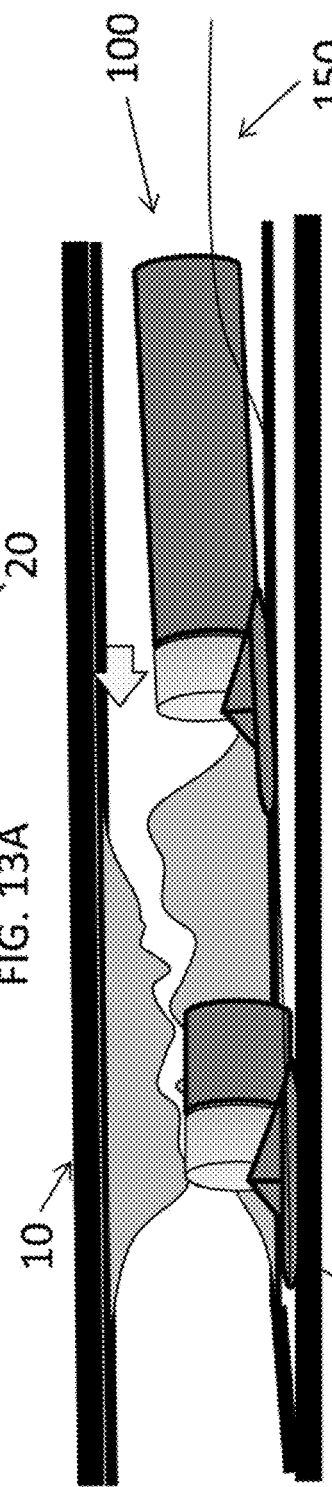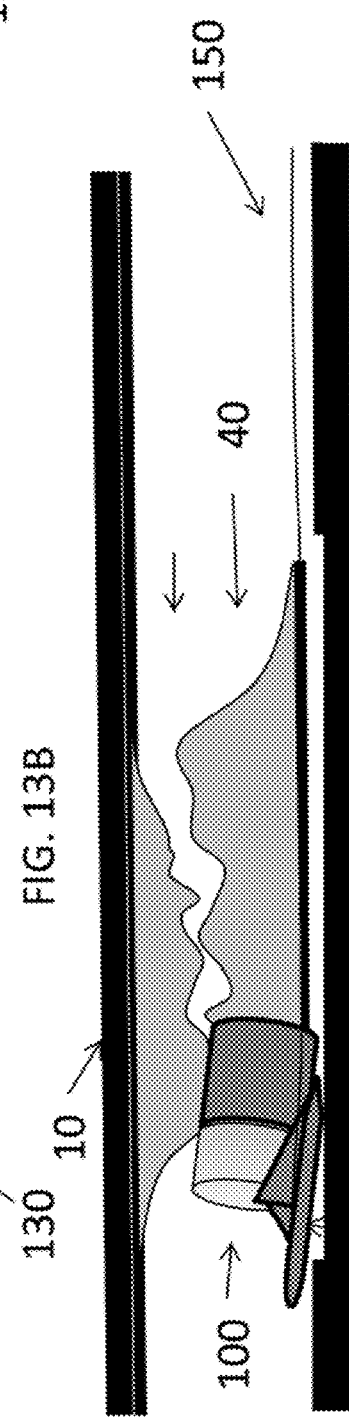

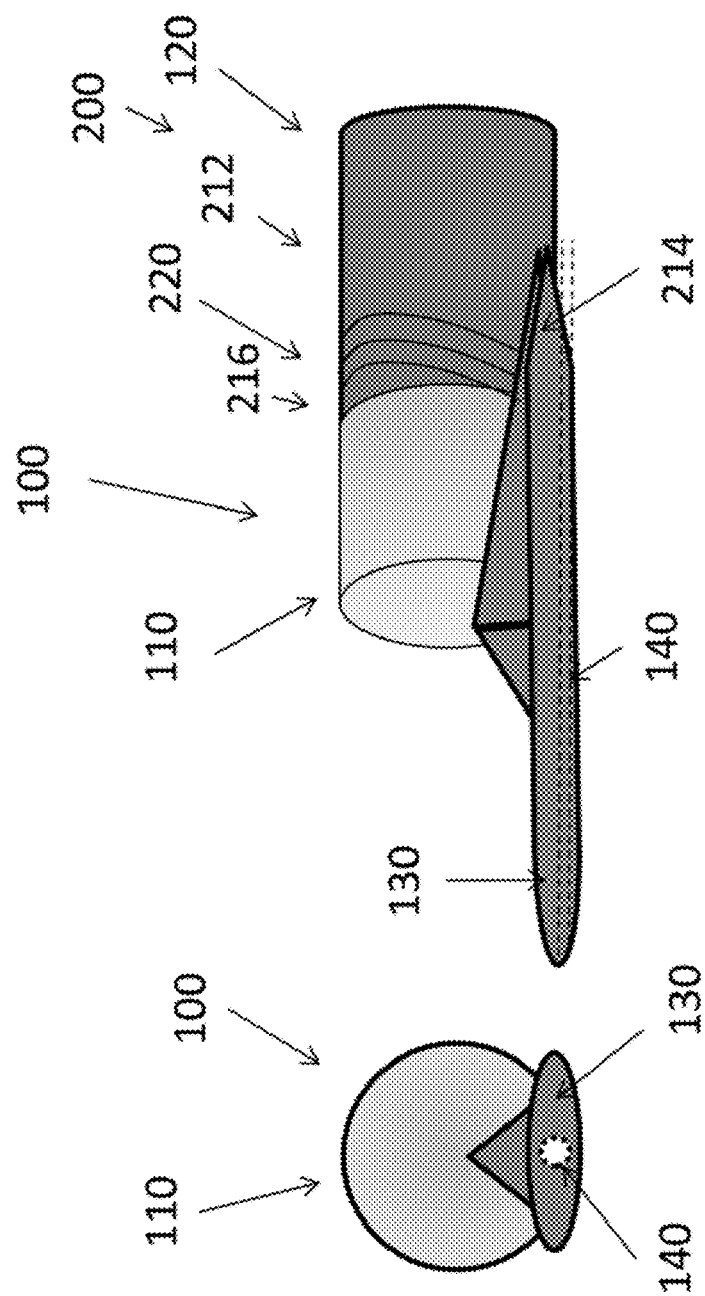

Pattern 1: Control with force

Under threshold

FIG. 15A

Over threshold

FIG. 15B 100
200
220
130
132

Pattern 2: Control with drive shaft

FIG. 15C 100
110
120
240
200

CW: extend → straight structure
CCW: shorten → bending structure

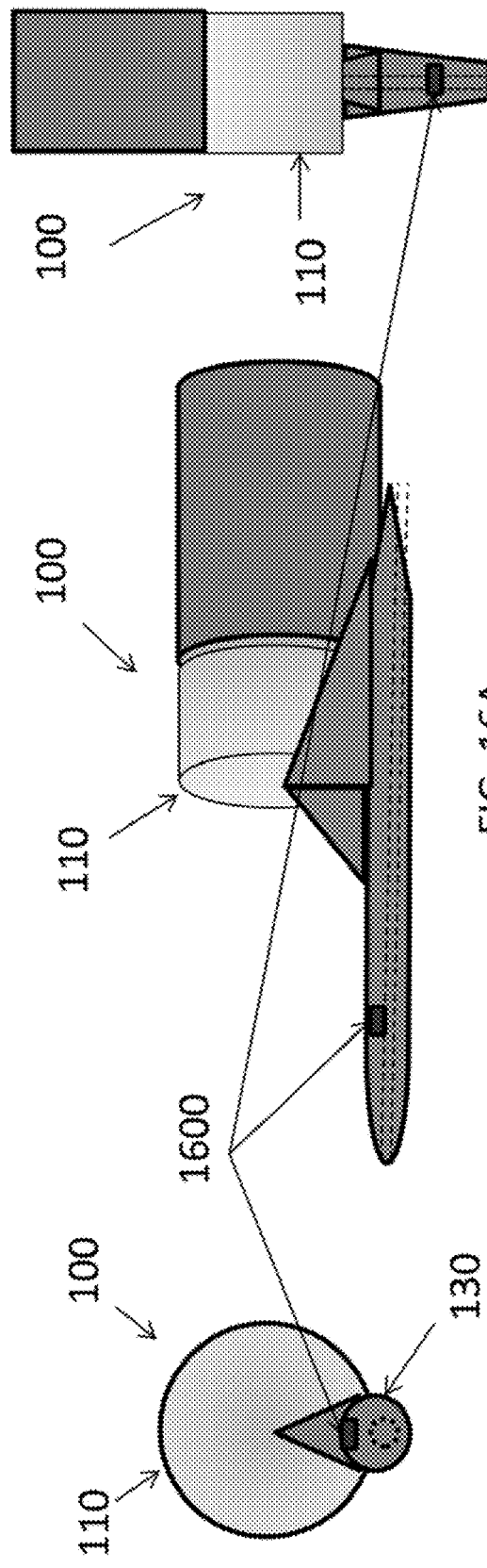
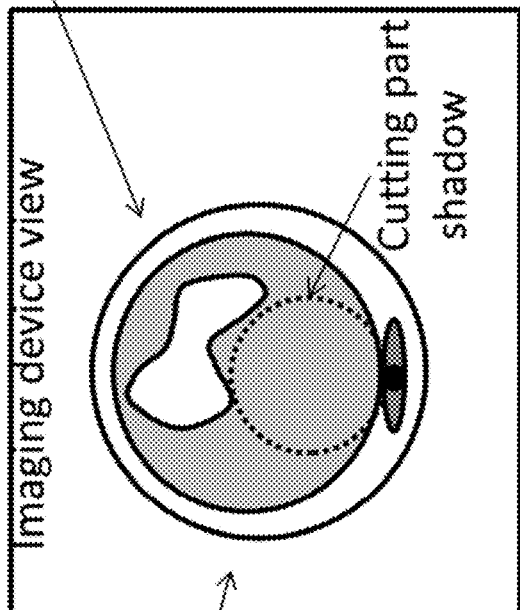
FIG. 16A
FIG. 16B
FIG. 16C
FIG. 16D
If the cutting part side is adventitia side, physician have to rotate the device to adjust cutting direction.

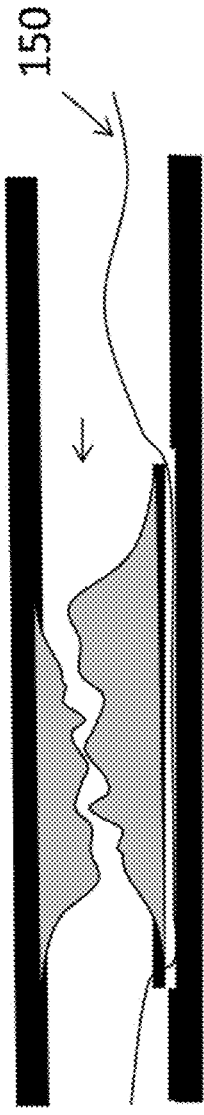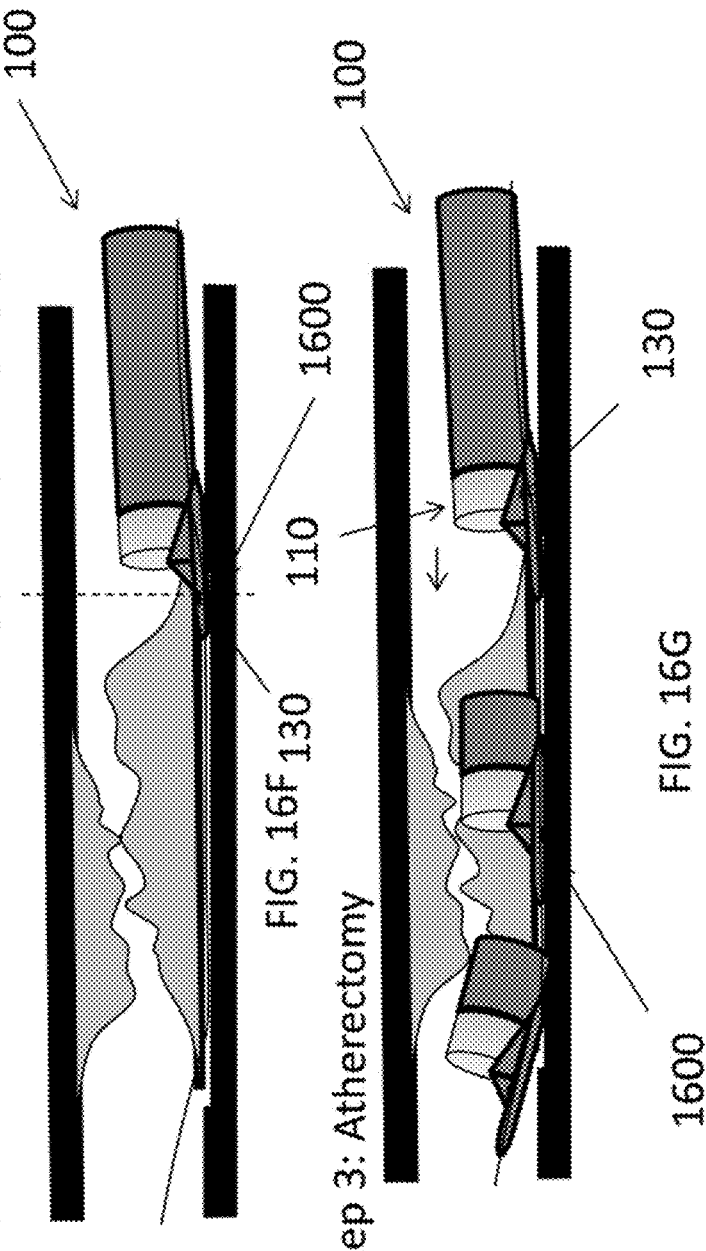

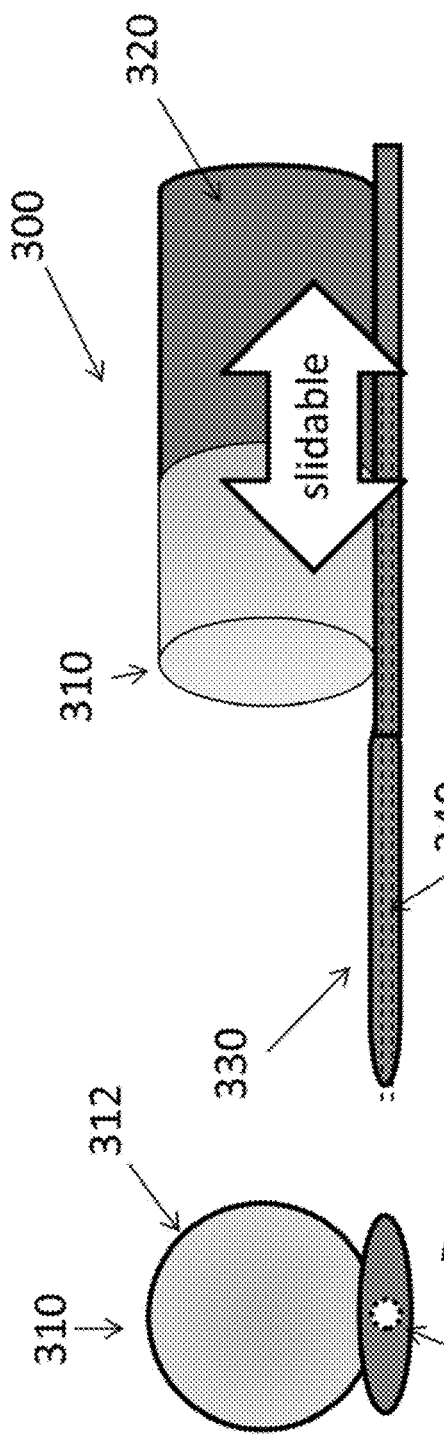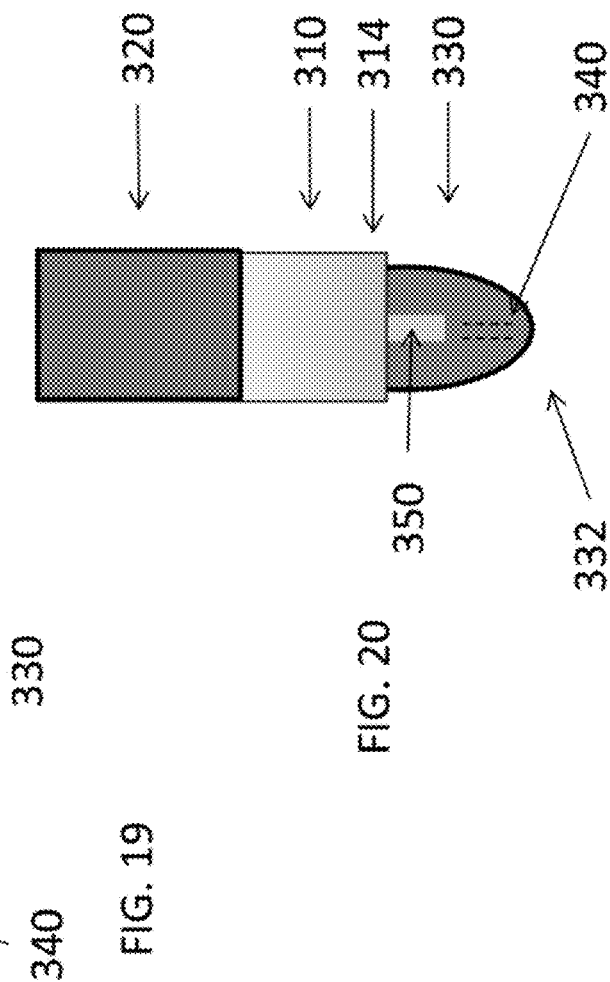

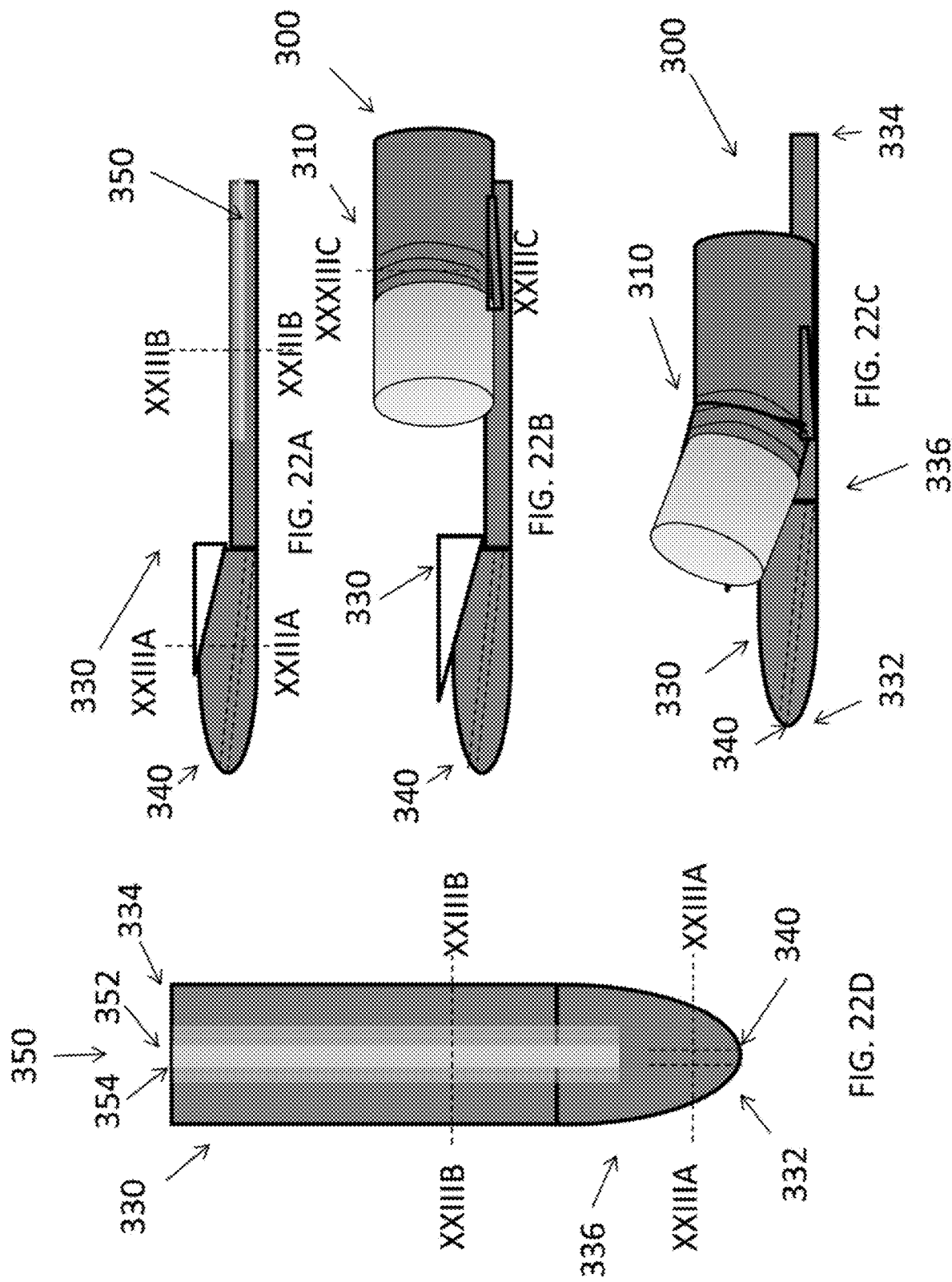

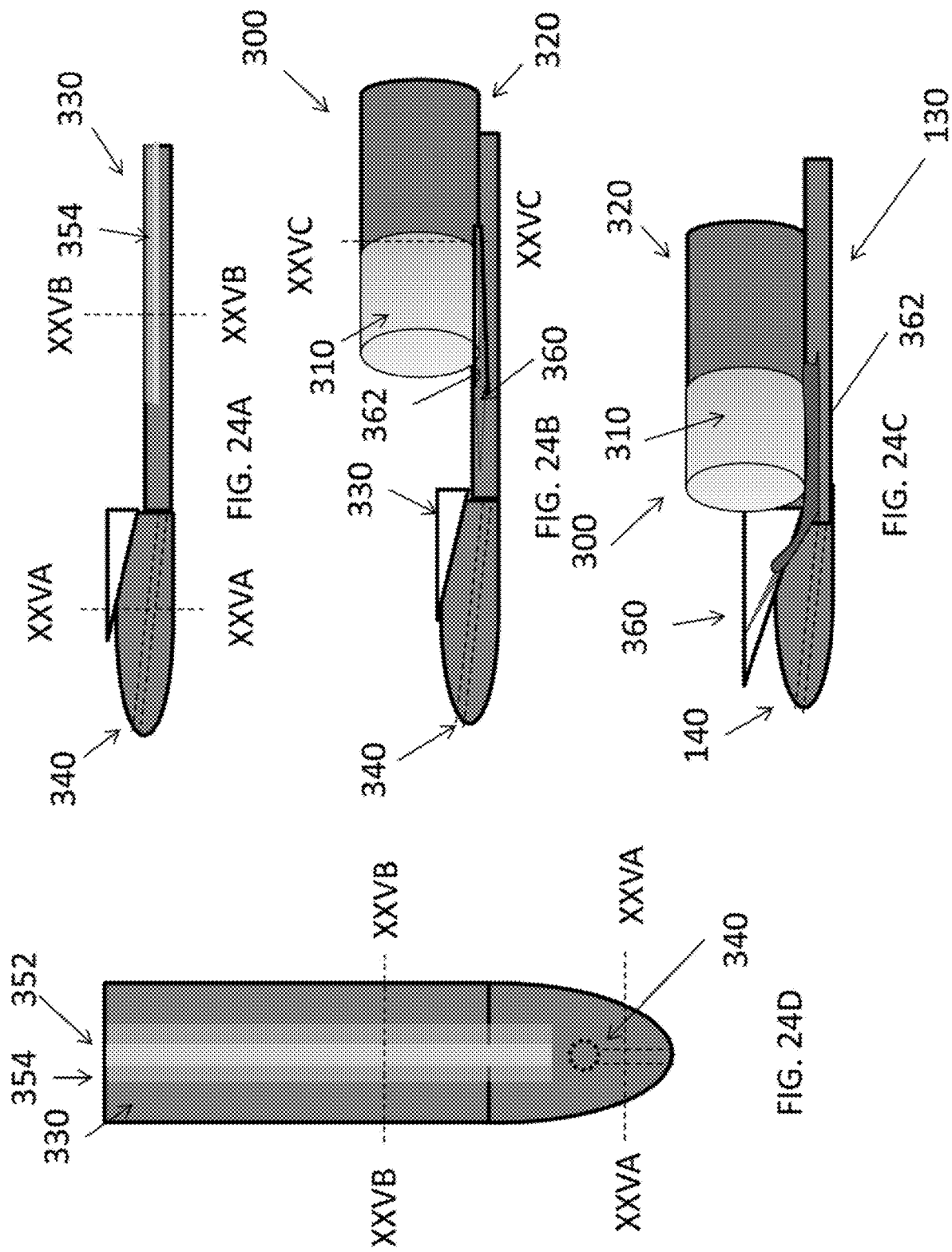

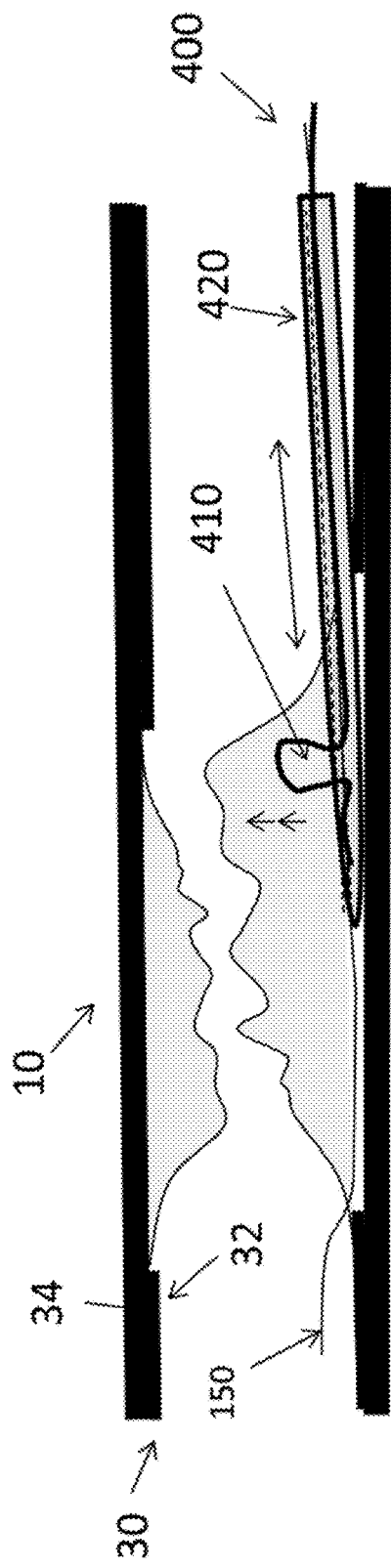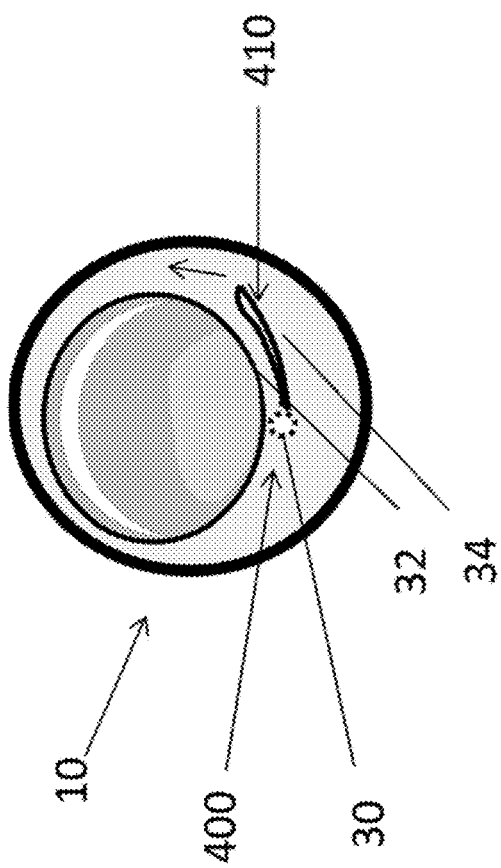

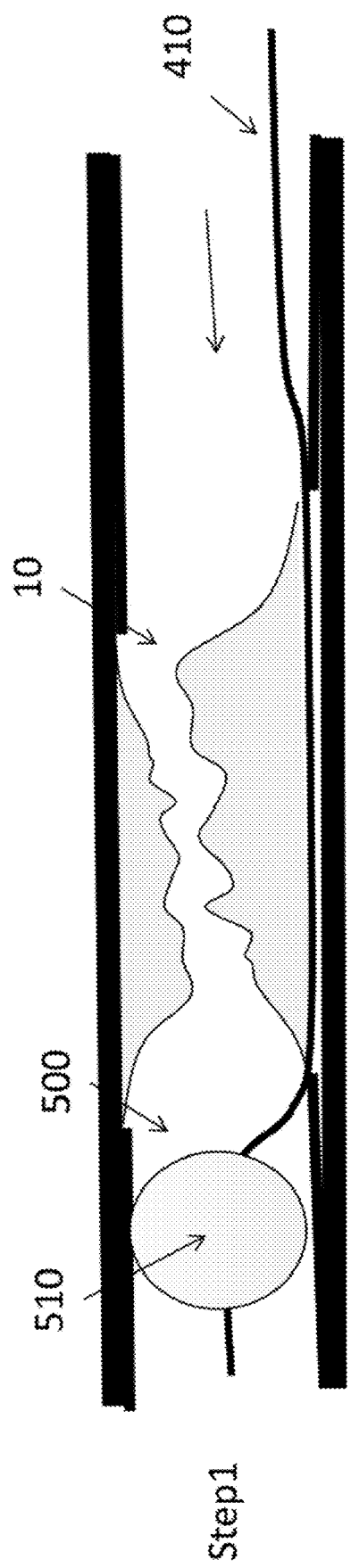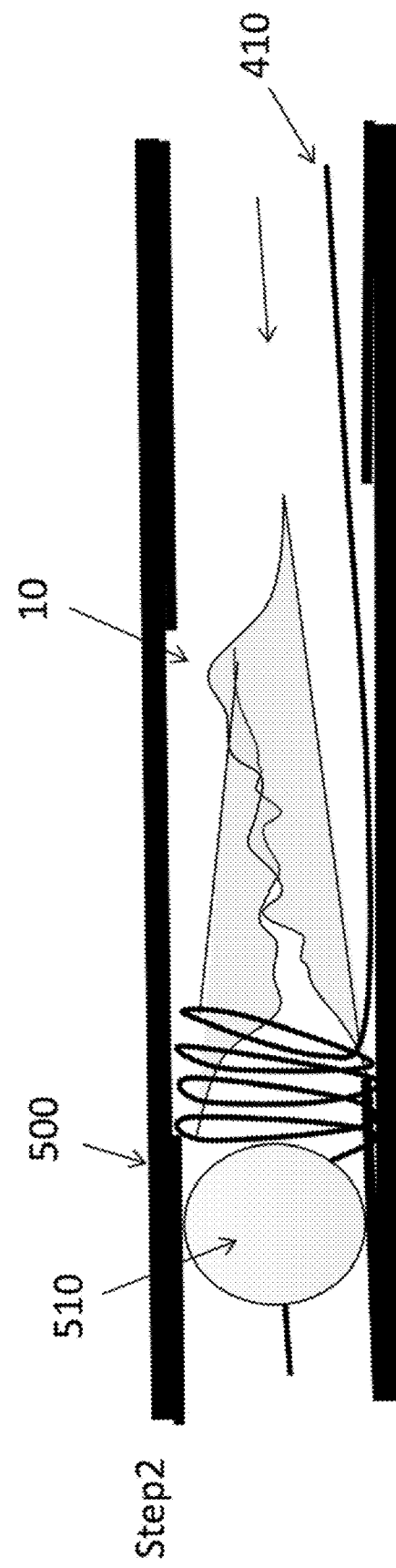
FIG. 28A
FIG. 28B

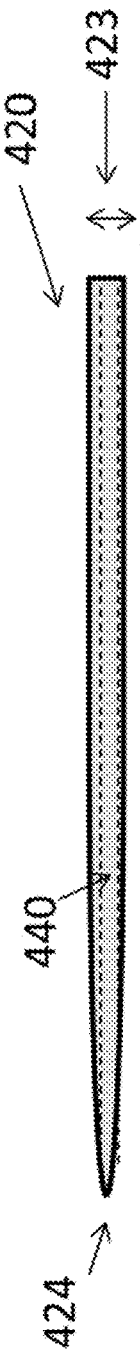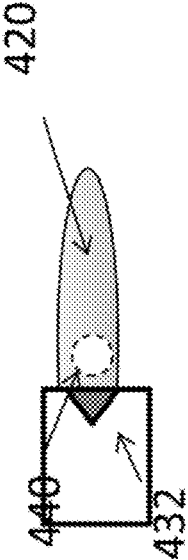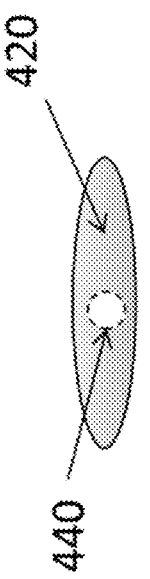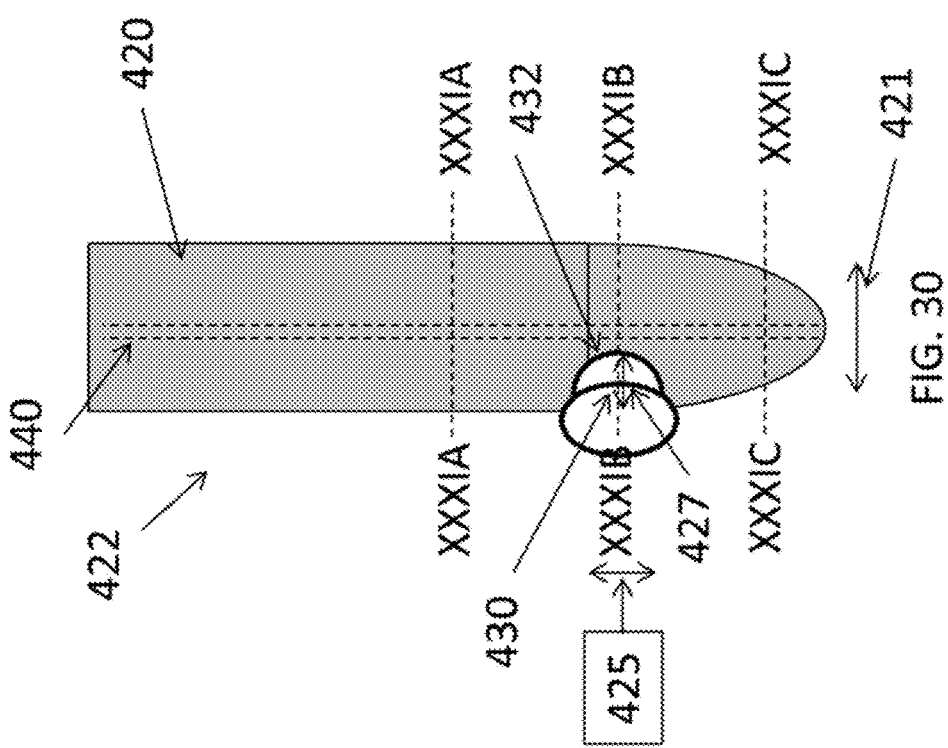

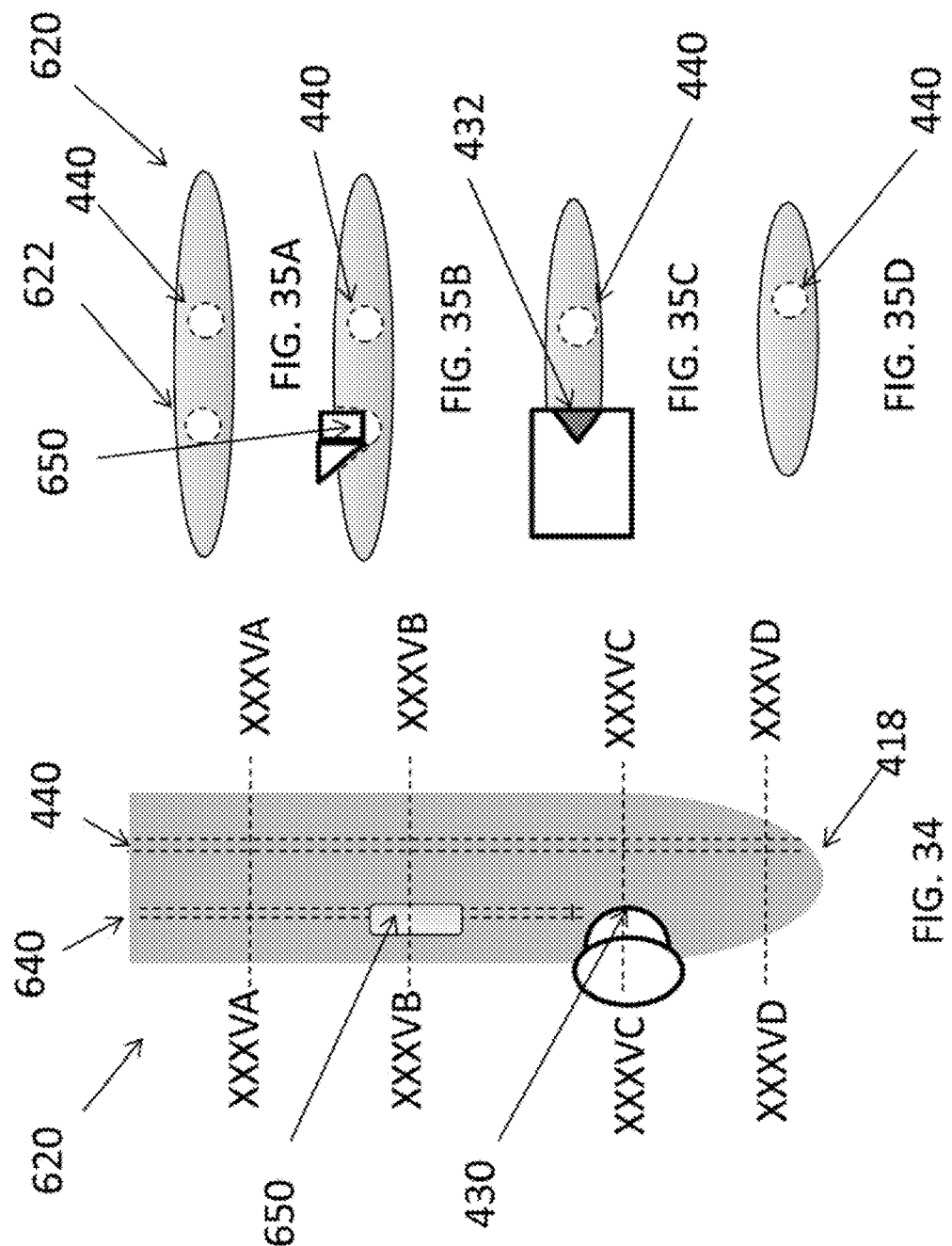

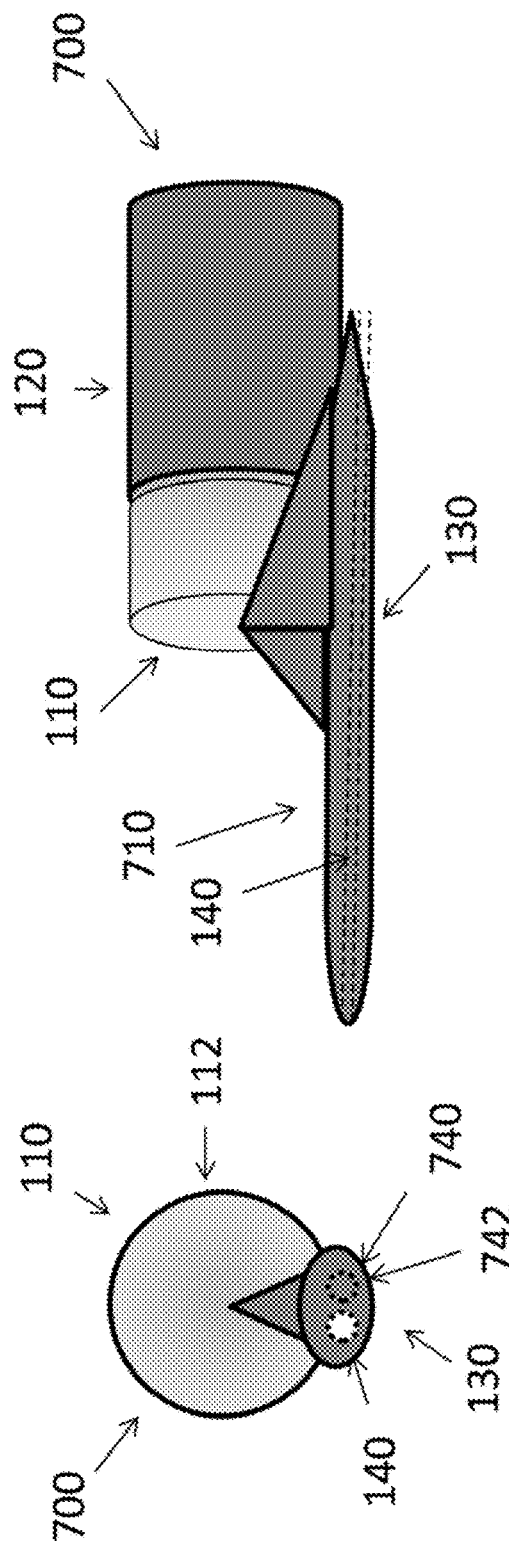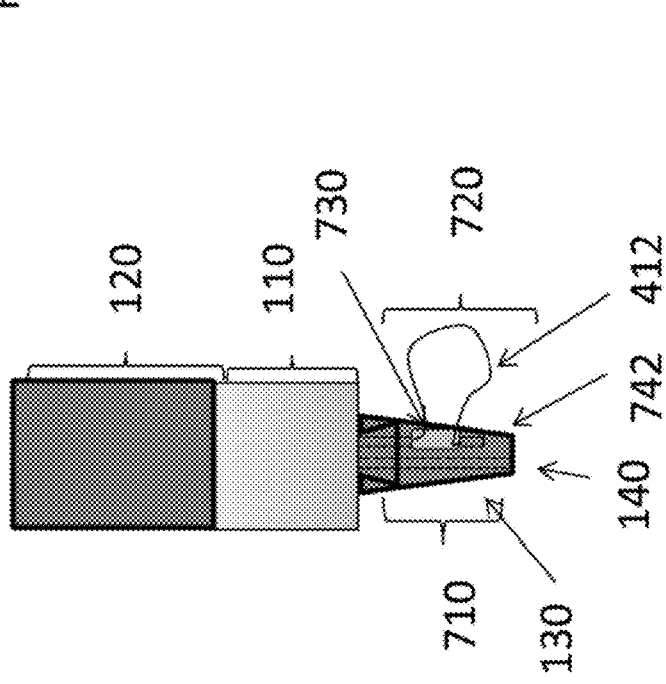
FIG. 37
FIG. 38
FIG. 39

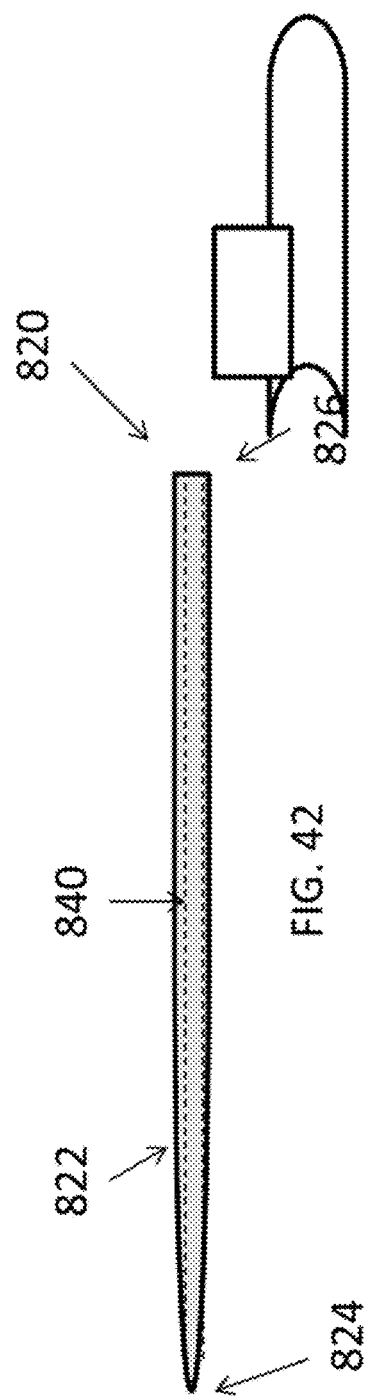

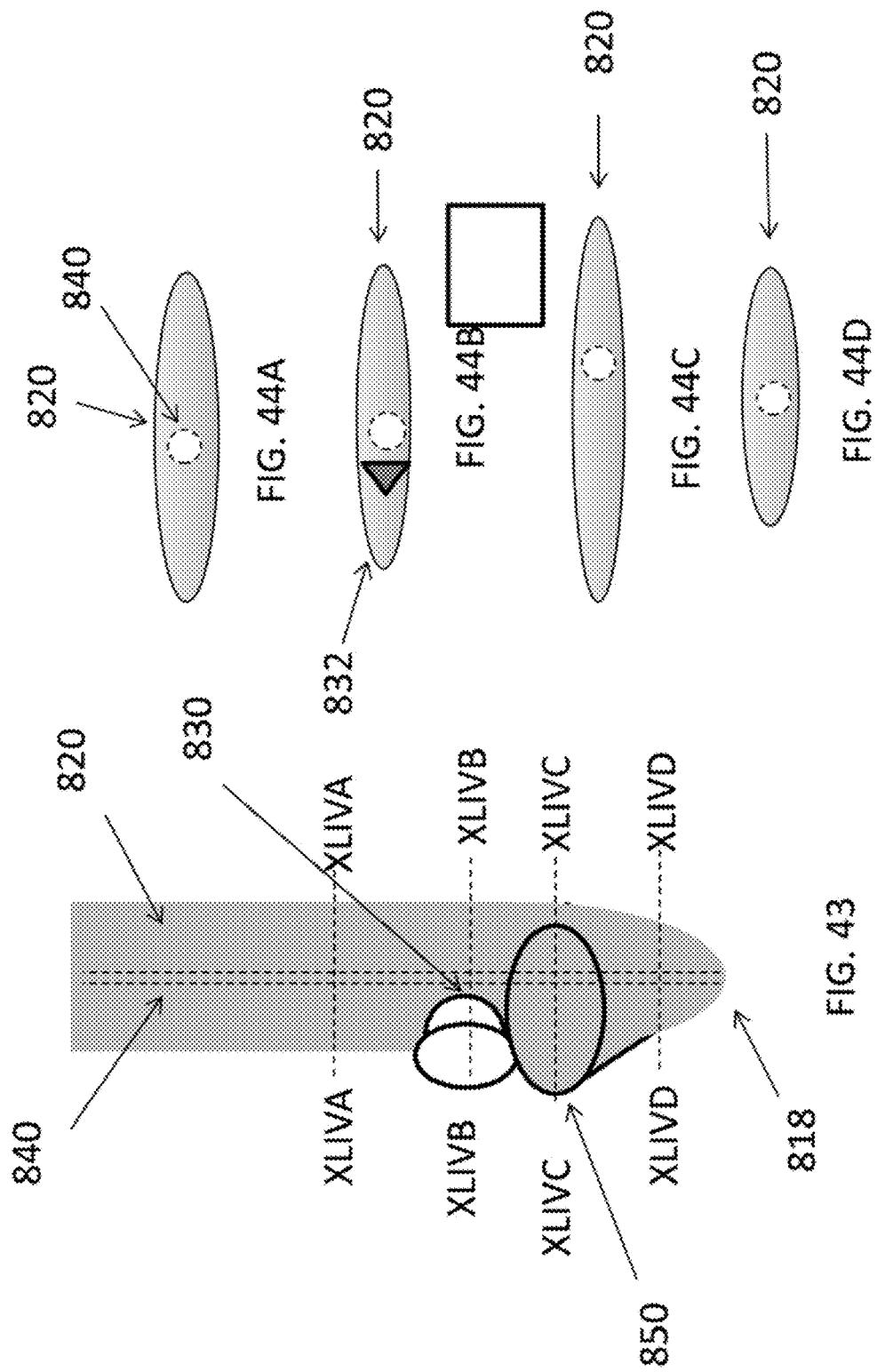

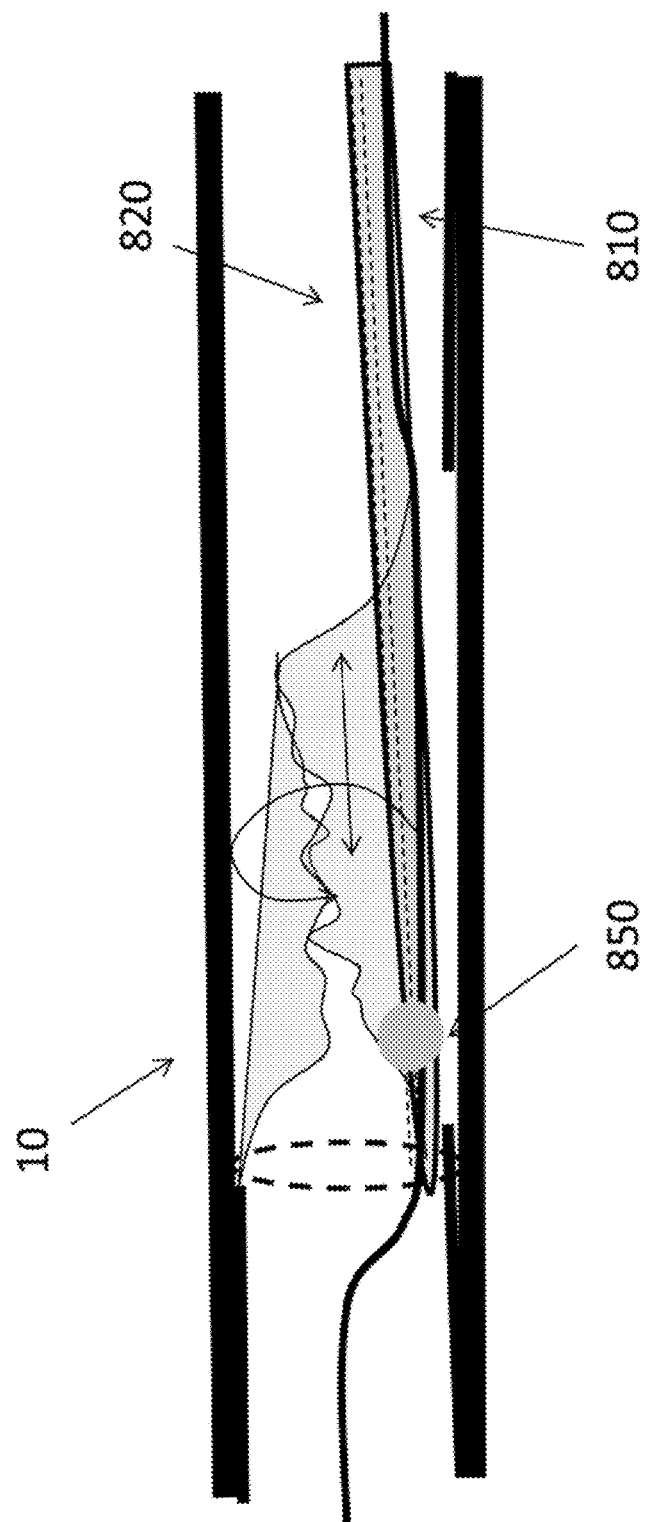

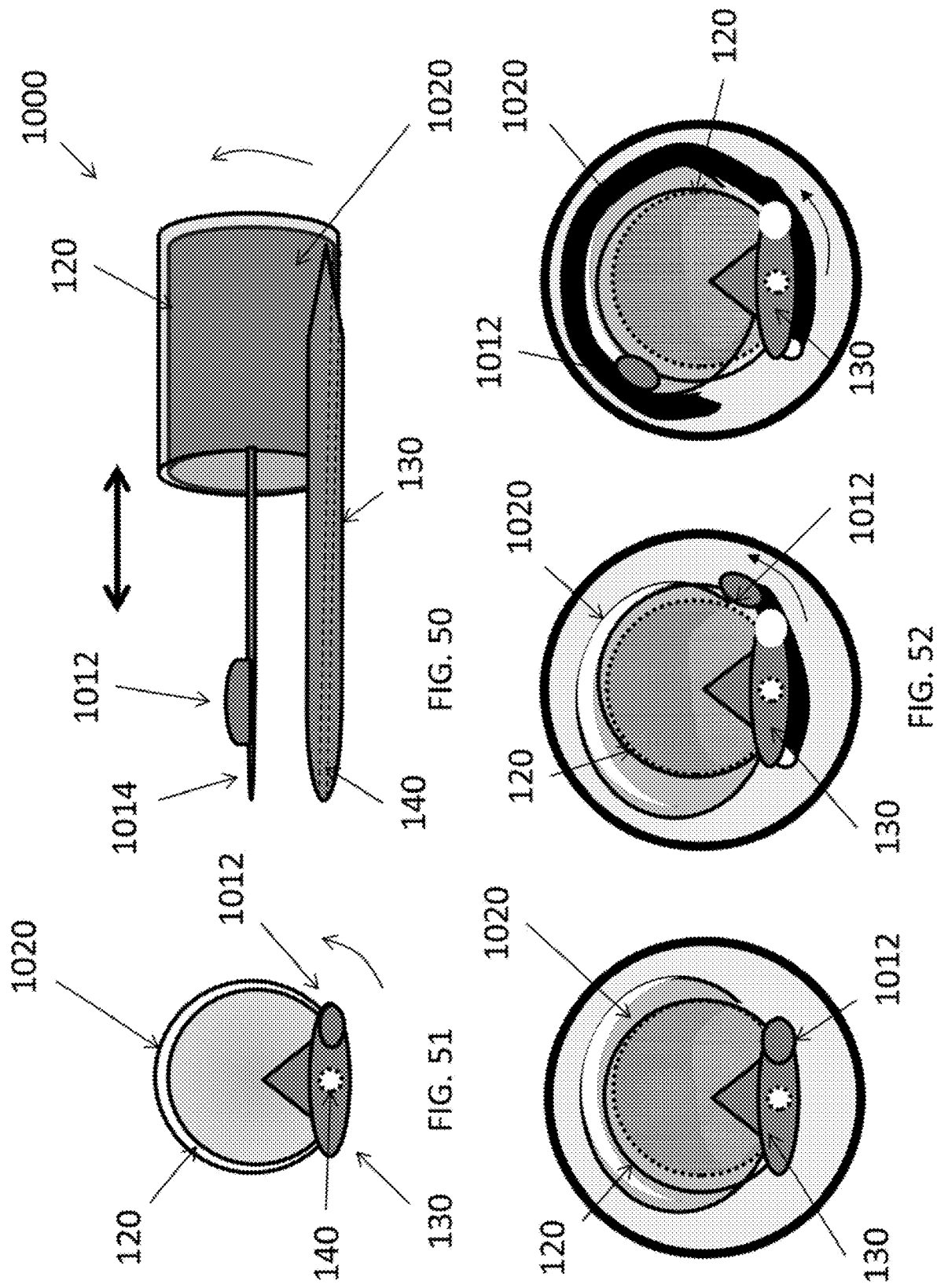

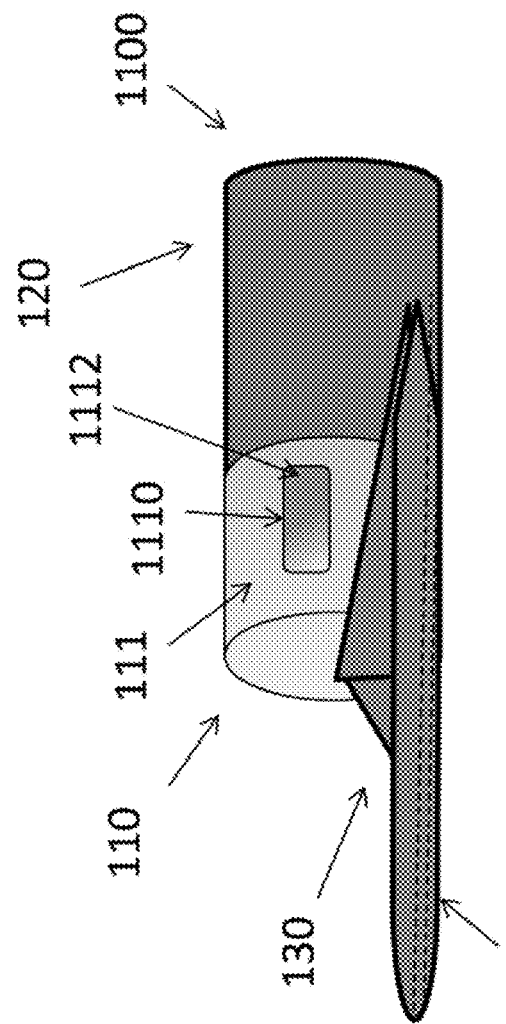
FIG. 53
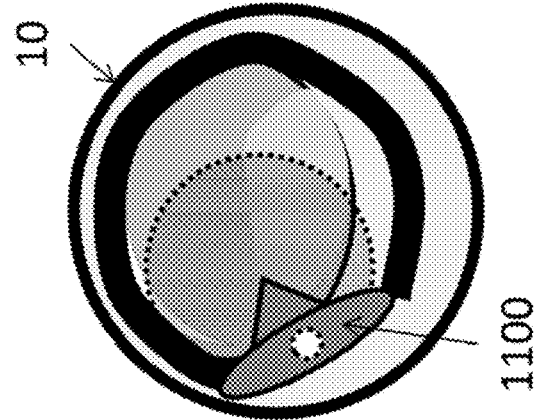
FIG. 54
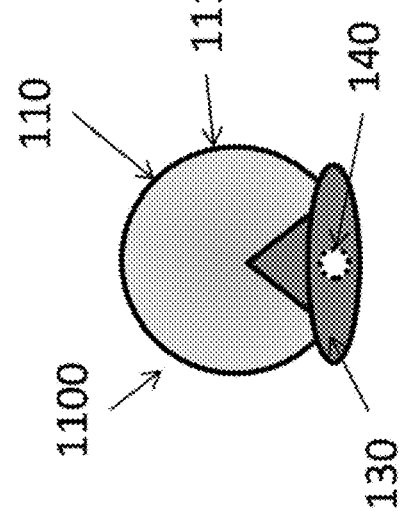
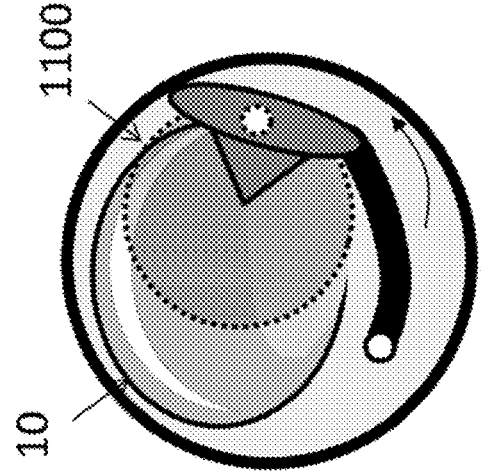
FIG. 55

ATHERECTOMY WITH SUBINTIMAL SPACE

TECHNICAL FIELD

The present disclosure generally relates to a medical device or dissecting device for cutting a substance from an inner wall surface of a body lumen, and more particularly, for treating a stenotic vessel with a dissecting device, which is inserted into a subintimal space from a blood vessel, and which cuts a stenotic region with the cutting member while advancing a directional guide member into the subintimal space.

BACKGROUND DISCUSSION

For physicians, it can be difficult to treat chronic total occlusion (CTO) and highly narrowing blood vessel regions due to difficulties associated with passing a guide wire before percutaneous transluminal angioplasty (PTA) and stent treatment. In these situations, physicians can perform a guide wire approach called the knuckle technique, for example, using, for example, a 0.035-inch wire with re-entry, for example, using a Rendez-vous technique. In these approaches, the guide wire is passed through and placed into the subintimal space.

A narrowed vessel can also be debulked by atherectomy to avoid the complications from PTA and stent treatment. However, physicians cannot always debulk the volume due to perforation risk during atherectomy treatment. In addition, other approaches include a true lumen wire approach, which can be time consuming since passing the wire through the true lumen can be difficult, and a subintimal wiring approach, which does not perform debulking by atherectomy.

Physicians can also perform a surgical treatment called endarterectomy to treated stenosis. In the femoral artery, for example, remote endarterectomy procedures are known. However, these procedures require large incisions to insert the medical devices and remove the intimal layer, which has been peeled off from the occluded vessel.

In view of the risks and difficulties with the known techniques, a less invasive technique is desirable, which can cut or debulk a stenotic region in only the true lumen side. In addition, it would be desirable, if the method and dissecting device can save time by avoiding trying to pass a wire through the true lumen, lower the risk of dissection and perforation during PTA and stenting from the subintimal space, and provide for re-entry during atherectomy.

SUMMARY

A method is disclosed for treating a stenotic vessel, the method comprising: inserting a first dissecting member into a subintimal space of a blood vessel and a second dissecting device configured to be received within a lumen within the first dissecting device and inserted into the blood vessel in a bent state; dissecting an inner side of the subintimal space from an outer side of the subintimal space over an entire circumference of the blood vessel with the first dissecting device; and removing the dissected inner side of the subintimal space and a stenotic region attached to the inner side of the subintimal space from the blood vessel.

A method is disclosed for treating a stenotic vessel, the method comprising: inserting a balloon wire into a subintimal space on a proximal side of a stenotic region and through the subintimal space to a distal side of the stenotic region, the balloon wire including a balloon and a wire; inflating the balloon of the balloon wire on the distal side of the stenotic region of the blood vessel; pushing the wire towards the inflated balloon and into the stenotic region; and dissecting an inner side of the subintimal space from an outer side of the subintimal space over an entire circumference of the blood vessel with the wire in a bent state.

A dissecting device is disclosed for treating a stenotic vessel, the dissecting device comprising: a first dissecting member for dissecting an inner side of a subintimal space from an outer side of the subintimal space over an entire circumference of the blood vessel, the first dissecting member having a cutting member on a distal end of the first dissecting member, which is configured to be rotated around the entire circumference of the blood vessel to separate the inner side of the subintimal space and the stenotic region from the outer side of the subintimal space.

BRIEF DESCRIPTION OF THE DRAWINGS

FIGS. 5A-5C is a perspective view, an end view, and a top view, respectively, of a dissecting device having a directional guide member with horizontal stabilization in accordance with an alternative exemplary embodiment.

FIGS. 6A-6C is a perspective view, an end view, and a top view, respectively, of a dissecting device in accordance with another alternative exemplary embodiment.

FIGS. 7A-7C is a perspective view, an end view, and a top view, respectively, of a dissecting device in accordance with a further exemplary embodiment.

FIGS. 8A-8C is a perspective view, an end view, and a top view, respectively, of a dissecting device as shown in FIGS. 7A-7C with a front force pushing into the subintimal space in accordance with an exemplary embodiment.

FIGS. 9A and 9B is a perspective view and an end view, respectively, of a dissecting device in accordance with a further embodiment of the first exemplary embodiment.

FIG. 10 is a plan view of the dissecting device of FIGS. 9A and 9B in accordance with an exemplary embodiment.

FIG. 11 is a plan view of the directional guide member having a tip as shown in FIG. 10 in an inactive state in accordance with an exemplary embodiment.

FIG. 12 is a plan view of the directional guide member as shown in FIG. 10 in an active state in accordance with an exemplary embodiment.

FIGS. 13A-13C are plan views of the dissecting device having a tip on the distal end of the directional guide wire as shown in FIGS. 9A-12.

FIG. 14A is a perspective view of a dissecting device having a bellow structure in accordance with an alternative embodiment of the first exemplary embodiment.

FIG. 14B is an end view of the dissecting device having a bellow structure as shown in FIG. 14A in accordance with an exemplary embodiment.

FIGS. 15A and 15B are perspective views of the dissecting device with a bellow structure as shown in FIGS. 14A and 14B under threshold and over threshold, respectively.

FIG. 15C is a perspective view of the dissecting device with a bellow structure as shown in FIGS. 14A and 14B with a coil type or coiled drive shaft in accordance with an exemplary embodiment.

FIGS. 16A-16C are a perspective view, an end view, and a top view, respectively, of the dissecting device, which includes the directional guide member, the cutting member, and an imaging guide for atherectomy in accordance with an exemplary embodiment.

FIG. 16D is a view on an imaging device, for example, an OCT/IVUS showing the dissecting device in use with the imaging portion or image sensor as shown in FIGS. 16A-16C.

FIGS. 16E-16G are plan views of subintimal wire spacing with the dissecting device and adjusting a direction of the cutting member with the imaging portion or image sensor in accordance with an exemplary embodiment.

FIG. 18 is a perspective view of the dissecting device as shown in FIG. 17 in accordance with an exemplary embodiment.

FIG. 19 is an end view of the dissecting device as shown in FIG. 18 in accordance with an exemplary embodiment.

FIG. 20 is a top view of the dissecting device as shown in FIGS. 18 and 19 in accordance with an exemplary embodiment.

FIG. 22A is a perspective view illustrating the directional guide member of a dissecting device having a cutting member with a bellow structure in accordance with an exemplary embodiment.

FIG. 22B is a perspective view illustrating the cutting member with a bellow structure of a dissecting device, which slides along the directional guide member in accordance with an exemplary embodiment.

FIG. 22C shows perspective views of the cutting device with a bellow structure of the dissecting device as shown in FIG. 22B, which slides along the directional guide member.

FIG. 22D is a top view of the guide member of the dissecting device as shown in FIGS. 22A-22C in accordance with an exemplary embodiment.

FIG. 24A is a perspective view illustrating the dissecting device with re-entry by a cutting member in accordance with another exemplary embodiment.

FIG. 24B is a perspective view illustrating the dissecting device with re-entry by cutting member in accordance with an exemplary embodiment.

FIG. 24C shows perspective views of the dissecting device with a bellow structure as the cutting member and tubular member slide along the guide member.

FIG. 24D is a top view of the guide member of the dissecting device as shown in FIG. 24A in accordance with the second exemplary embodiment.

FIG. 26 is a plan view of a dissecting system in accordance with an exemplary embodiment in which a dissecting member is shown in a bent state in accordance with a third exemplary embodiment.

FIG. 27 is a cross-sectional view of a blood vessel as shown in FIG. 26 in which the dissecting member is in a bent state in accordance with the third exemplary embodiment.

FIGS. 28A and 28B are plan views of the dissecting member as a balloon wire within a blood vessel in accordance with an exemplary embodiment.

FIG. 29 is a plan view of a cutting device in accordance with an exemplary embodiment.

FIG. 30 is a top view of the cutting device of FIG. 29 in accordance with an exemplary embodiment.

FIGS. 31A-31C are a series of cross-sectional views of the cutting device of FIG. 30 along the lines XXXIA-XXXIA, XXXIB-XXXIB, and XXXIC-XXXIC, respectively, in accordance with an exemplary embodiment.

FIG. 34 is a top view of the cutting device of FIG. 33 in accordance with an exemplary embodiment.

FIGS. 35A-35D are a series of cross-sectional views of the cutting device of FIG. 34 along the lines XXXVA-XXXVA, XXXVB-XXXVB, XXXVC-XXXVC, and XXXVD-XXXVD, respectively, in accordance with an exemplary embodiment.

FIG. 37 is a perspective view of a dissecting device having a dissecting member in the form of a dissecting member or loop and a cutting member in accordance with an exemplary embodiment.

FIG. 38 is an end view of the dissecting device as shown in FIG. 37 in accordance with an exemplary embodiment.

FIG. 39 is a top view of the dissecting device as shown in FIGS. 37 and 38 in accordance with an exemplary embodiment.

FIG. 42 is a perspective view of a cutting device of the dissection device shown in FIG. 41 in accordance with an exemplary embodiment.

FIG. 43 is a top view of the cutting device of FIG. 42 in accordance with an exemplary embodiment.

FIGS. 44A-44D are a series of cross-sectional views of the cutting device of FIG. 43 and cross-sectional view along the lines XLIVA-XLIVA, XLIVB-XLIVB, XLIVC-XLIVC, and XLIVD-XLIVD, respectively, in accordance with an exemplary embodiment.

FIG. 45 is a plan view of the dissecting member as shown in FIGS. 42-44D in accordance with an exemplary embodiment.

FIG. 50 is a perspective view of a dissecting device in accordance with an alternative exemplary embodiment.

FIG. 51 is an end view of the dissecting device as shown in FIG. 50 in accordance with an exemplary embodiment.

FIG. 52 is series of end views showing the dissecting device as shown in FIGS. 50 and 51 in a blood vessel having a stenosed region.

FIG. 53 is a perspective view of the dissecting device in accordance with an exemplary embodiment.

FIG. 54 is an end view of the dissecting device as shown in FIG. 53 in accordance with an exemplary embodiment.

FIG. 55 is series of end views showing the dissecting device as shown in FIGS. 53 and 54 in a blood vessel having a stenosed region.

DETAILED DESCRIPTION

Figure 1:
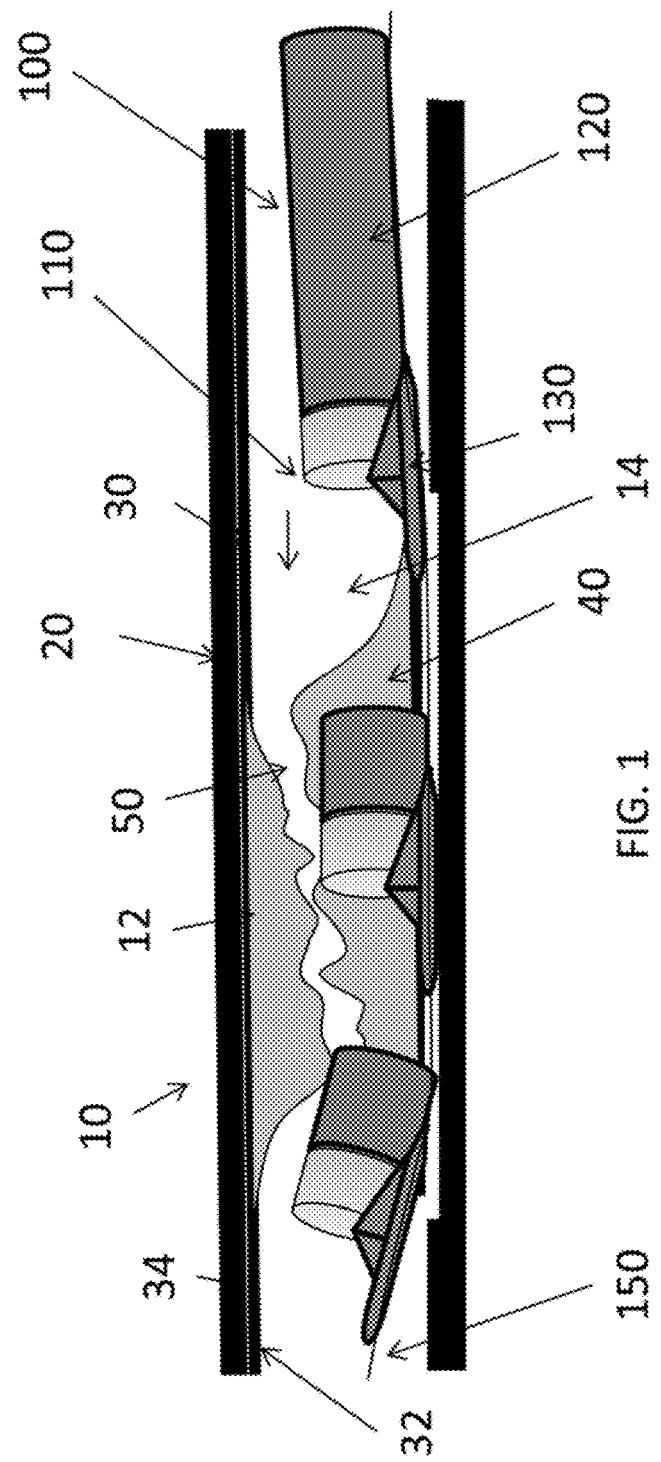
FIG. 1 is a schematic view illustrating a medical device (or a dissecting device), which includes a directional guide member and a cutting member, which advance together in accordance with a first exemplary embodiment.

Hereinafter, embodiments of the present disclosure will be described with reference to the drawings. In order to facilitate description, dimensional ratios in the drawings are exaggerated, and thus are different from actual ratios in some cases.

FIG. 1 is a schematic view illustrating a medical device (or dissecting device) 100, which includes a directional guide member 130 and a tubular cutting member 110, which advance together in accordance with a first exemplary embodiment. As shown in FIG. 1, the medical device or dissecting device 100 is guided into the subintimal (or intima space) 30 of the blood vessel 10 with the directional guide member 130 and the stenosed region 12 is cut with the cutting member 110 of the dissecting device 100. Advantageously, the medical device or dissecting device 100 as disclosed herein can cut a stenotic region 40 in only a true lumen side 50. In addition, the medical device or dissecting device 100 by cutting the stenosed site 40 can safely perform the atherectomy from a subintimal space (or outer intimal layer), which enables the dissecting device 100 to increase a size of the lumen 14 of the blood vessel 10 for improved blood flow.

The medical device 100 according to the first embodiment of the present disclosure can be used for therapy (treatment) to cut a stenosed site or an occluded site 12 which can be caused by a plaque, a fibrotic plaque, calculus, a blood clot, or a thrombus 40 inside the blood vessel 10. In this description, a side of the device 100, which is inserted into the blood vessel 10, is referred to as a "distal side" or "distal end", and an operating hand side is referred to as a "proximal side" or "proximal end". The blood vessel (or artery) 10 comprises the tunica adventitia (or adventitia for short), which is the outermost tunica (layer) of a blood vessel 10, and surrounds the tunics media (or media), which is the middle layer of the blood vessel or artery. Reference number 20 collectively identifies the adventitia and the media. As shown, the subintimal (or intima) 30 is the inner most layer of the blood vessel or artery 10, and is surrounded by the adventitia and the media 20. The subintimal 30 has an inner surface or inner side 32 and an outer surface or outer side 34.

Figure 2:
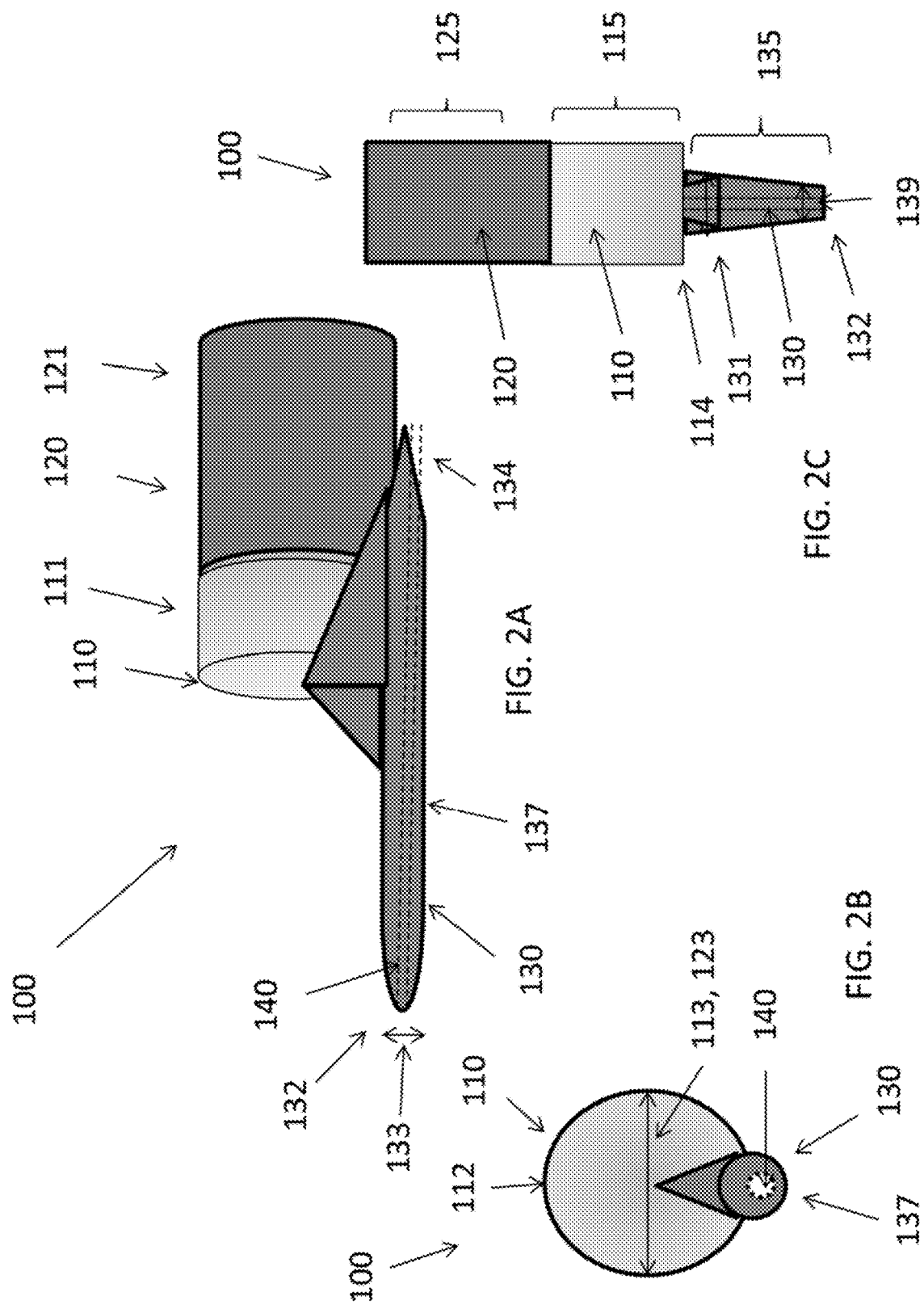
FIG. 2A is a perspective view of the dissecting device in accordance with the first exemplary embodiment.
FIG. 2B is an end view of the dissecting device as shown in FIG. 2A in accordance with an exemplary embodiment.
FIG. 2C is a top view of the dissecting device as shown in FIGS. 2A and 2B in accordance with an exemplary embodiment.

FIG. 2A is a perspective view of the dissecting device 100 in accordance with the first exemplary embodiment. As shown in FIG. 2A, the dissecting device includes a directional guide member 130 having a wire lumen 140 therein configured to receive a guide wire 150. The dissecting device 100 also includes the cutting member 110 and the tubular member 120, which is located on the proximal side of the cutting member 110. In accordance with an exemplary embodiment, the directional guide member 130 is located on a distal side of the cutting member 110 and the tubular member 120. The cutting member 110 and the tubular member 120 preferably has an oval or round outer diameter 111, 121 having a similar radius of curvature of a blood vessel 10 so that during cutting of the stenosed region 40, the cutting member 110 and tubular member 120 do not rotate within the blood vessel 10.

In accordance with an exemplary embodiment, a lower surface 137 of the directional guide member 130 can be relatively flat, can have convex or round shape, which generally mirrors an inner diameter of the blood vessel 10. Alternatively, in accordance with an exemplary embodiment, at least a distal portion of the directional guide member 130 can rotates about a central axis (not shown) thereto with a relatively flat or slight upward trend, for example, trending upward from the proximal end 134 to the distal end 132 at an angle of less than about 30 degrees, and more preferably about 10 to 25 degrees.

FIG. 2B is an end view of the dissecting device 100 as shown in FIG. 2A in accordance with an exemplary embodiment. As shown in FIG. 2B, a cutting edge 112 of the cutting member 110 has a generally oval or round shape thereto. In accordance with an exemplary embodiment, the directional guide member 130 can have a rounded distal end with a guide wire lumen 140. In accordance with an exemplary embodiment, the directional guide member 130 can have a rounded outer diameter, which generally is narrowed at the distal end of the guide member 130 and expands outward moving a proximal direction towards the cutting member 110.

FIG. 2C is a top view of the dissecting device 100 as shown in FIGS. 2A and 2B in accordance with an exemplary embodiment. As shown in FIG. 2C, the directional guide member 130 extends from a distal end 114 of the cutting member 110 having a greater width at a proximal end extending to a distal end or tip of the guide member 130. In accordance with an exemplary embodiment, the proximal end of the directional guide member 130 and at least a proximal portion of the directional guide member 130 are located on an outer surface of the cutting member 110. The directional guide member 130 can have a width 131, for example, of about 1.2 mm to 6.0 mm at a proximal end 134 and a width 139, for example, of about 0.40 mm to 1.2 mm at distal end of the cutting member 110, a thickness 133, for example, of about 0.40 mm to 2.0 mm, and a length 135, for example, of about 3.0 mm to 30 mm.

In accordance with an exemplary embodiment, an outer diameter 111, 121 of the cutting member 110 and the tubular member 120 can be between about 1.0 mm to about 6.0 mm in diameter. An inner diameter 113, 123 of the cutting member 110 and the tubular member 120 can be, for example, between about 0.8 mm to about 5.9 mm in diameter. In addition, the cutting member 110 can have a length 115 of, for example, about 1.0 mm to 15 mm, and the tubular member 120 can have a length 125 of, for example, about 150 mm to 3000 mm.

Figure 3:
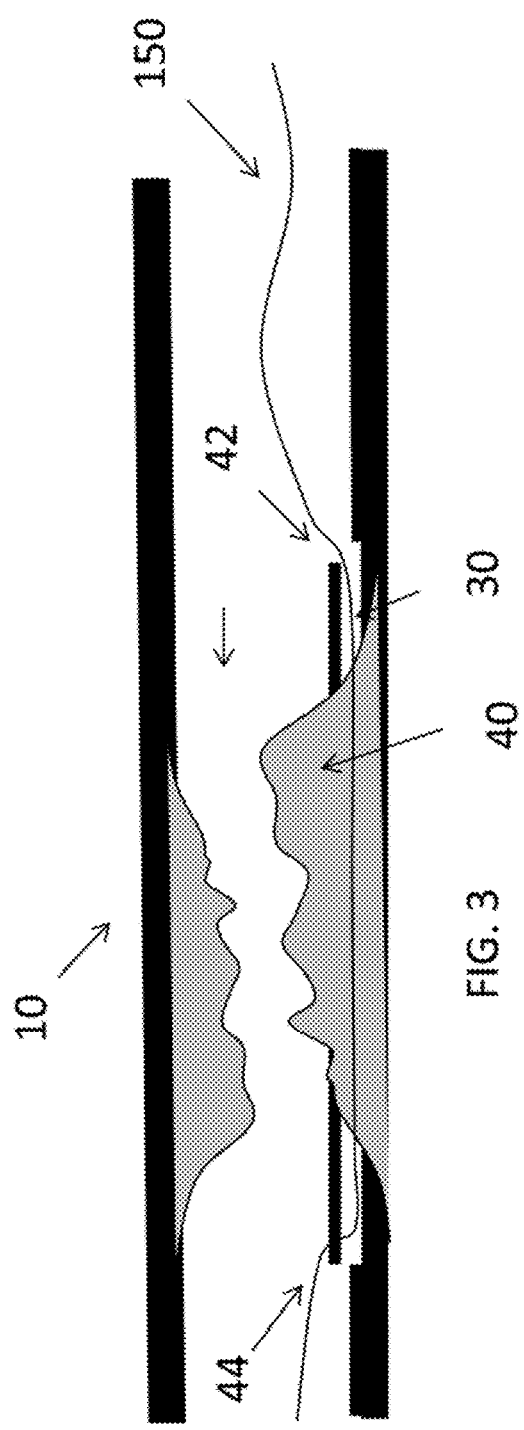
FIG. 3 is a plan view illustrating a guide wire in a stenosed site with a subintimal space wiring with re-entry in accordance with an exemplary embodiment.

FIG. 3 is a plan view illustrating a guide wire 150 in a stenosed site 12 with a subintimal space wiring with optional re-entry in accordance with an exemplary embodiment. In accordance with an exemplary embodiment, as shown in FIG. 3, a guide wire 150 can be inserted into a subintimal space 30 within the blood vessel 10, for example, entering the subintimal space on a proximal side 42 of the stenosis 40 and exiting from subintimal space on a distal side 44 of the stenosis 40.

Figure 4:
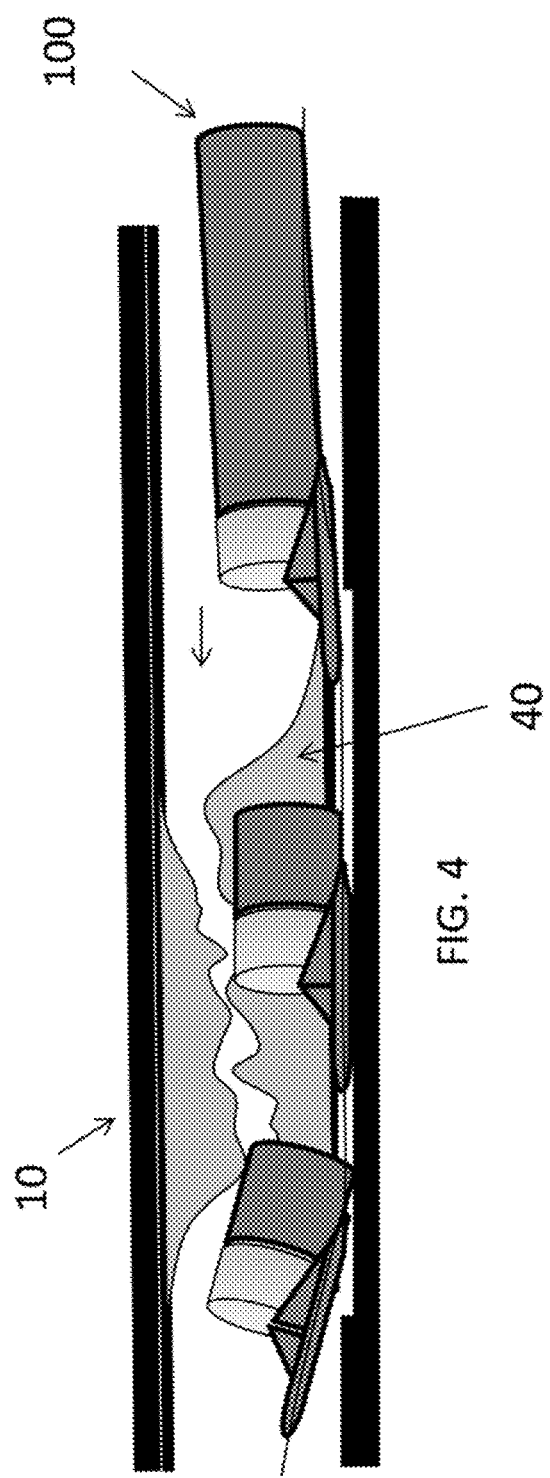
FIG. 4 is a plan view illustrating the dissecting device in the stenosed site performing the atherectomy of the stenosis in accordance with an exemplary embodiment.

FIG. 4 is a plan view illustrating the dissecting device 100 in the stenosed site 12 performing the atherectomy of the stenosis 40 in accordance with an exemplary embodiment. As shown in FIG. 4, the dissecting device 100 is placed on the guide wire 150 and moves from the proximal end 42 of the stenosis 40 through the stenosis 40 to the distal end 44 of the stenosis 40 cutting out the stenosis 40 as the dissecting device 100 moves distally. The stenosis 40 that has been cut is then removed from the blood vessel 10 in each of the exemplary embodiments.

FIGS. 5A-5C is a perspective view, an end view, and a top view, respectively, of a dissecting device 100 having a directional guide member 130 with horizontal stabilization 160 in accordance with an alternative exemplary embodiment. As shown in FIGS. 5A-5C, the directional guide member 130 has a pair of flanges 162, which extends radially outward from each of side edge 164 of the guide member 130. In accordance with an exemplary embodiment, the pair of flanges 162 has a curvature thereto such that the directional guide member 130 has a radially extending convex shape thereto. Alternatively, the pair of flanges 162 can be relatively flat or horizontal forming a relatively radially extending flat structure, for example, as shown in FIGS. 6A-6C.

FIGS. 6A-6C is a perspective view, an end view, and a top view, respectively, of a dissecting device 100 in accordance with another alternative exemplary embodiment. As shown in FIGS. 6A-6C, the directional guide member 130 can be a relatively flat or horizontal plate 170 having an outer edge 172 which generally has a round or oval shape. Alternatively, as shown in FIGS. 6A-6C, the outer edges 172 of the plate 170 can be slightly curved radially extending upward such that the horizontal plate 170 has a convex shape (FIG. 5).

FIGS. 7A-7C is a perspective view, an end view, and a top view, respectively, of a dissecting device 100 in accordance with a further exemplary embodiment. As shown in FIGS. 7A-7C, the directional guide member 130 includes a micro blade (or vertical stabilizer) 180, which provides vertical stabilization to the directional guide member 130 and an elastomeric cover 190 which covers a portion of the micro blade 180 such that a tip or edge 182 of the micro blade 180 does not protrude through a distal portion or distal surface 192 of the elastomeric cover 190 in a non-compressed state, for example, with the absence of a front force caused by pushing the dissecting device 100 through the stenosed site 40. In accordance with an exemplary embodiment, the elastomeric cover 190 can be made from silicone, polyurethane, or latex. In accordance with an exemplary embodiment, for example, the elastomeric cover 190 can be a blade spring, for example, a metal spring.

In accordance with an exemplary embodiment, the cutting member 110 can be made of stainless steel (SUS), Nickel titanium alloy or Nitinol (NiTi), tungsten carbide (WC), or high-speed steel. The tubular member 120 can be made of polyimide, polyether ether ketone (PEEK), nylon, polyurethane, blade-tube, for example, a weaved tube with a composite of weaved wire and polymer, metal coil covered by heat shrink tube, or composed of a combination of these material. The directional guide member 130 can be stainless steel (SUS), polyimide, Peek, Nylon, polyurethane, or composed of a combination of these materials.

FIGS. 8A-8C is a perspective view, an end view, and a top view, respectively, of a dissecting device 100 as shown in FIGS. 7A-7C with a front force pushing into the subintimal space in accordance with an exemplary embodiment. As shown in FIGS. 8A-8C, upon a force, for example, upon being pushed or forced through the subintimal space 30, the distal end 192 of the elastomeric material 190 moves proximally, which exposes the tip or edge 182 of the micro blade 180. As shown, upon application of a force 60 to the elastomeric material 190, the micro blade 180 extends to distal side of the elastomeric material 190.

FIGS. 9A and 9B is an end view and a perspective view, respectively, of a dissecting device 100 in accordance with a further embodiment of the first exemplary embodiment. As shown in FIGS. 9A and 9B, the distal end 132 of the directional guide member 130 has a tip 200, which is placed in front (or distally) of the cutting member 110. In accordance with an exemplary embodiment, the tip 200 can be relatively flat with a sharp edge or point. In accordance with an exemplary embodiment, the directional guide member 130 is preferably angled upwards, for example, extending upwards from a proximal end 134 of the directional guide member 130 towards the distal end 132. The tip 200 is preferably located on a lower surface 136 of the directional guide member 130 just beneath the guide wire lumen 140. In accordance with an exemplary embodiment, the distal end 202 of the tip 200 can be angled upward and having a convex lower surface 204, for example, as a crescent moon like shape.

FIG. 10 is a plan view of the dissecting device 100 of FIGS. 9A and 9B in accordance with an exemplary embodiment. As shown in FIG. 10, the tip 200 is located on the distal end 132 of the directional guide member 130 just below or beneath the guide wire lumen 140 on the lower surface 137 of the directional guide member 130. In accordance with an exemplary embodiment, the tip 200 is preferably made of a material having sufficient hardness to break through the subintimal space 30. In accordance with an exemplary embodiment, the tip 200 can be made of a metal, for example, stainless steel (SUS), Nickel titanium alloy or Nitinol (NiTi), tungsten carbide (WC), or high-speed steel, or a polymer, for example, polyimide, polyether ether ketone (PEEK), nylon, or polyurethane.

FIG. 11 is a plan view of the directional guide member 130 having a tip 200 as shown in FIG. 10 in an inactive state in accordance with an exemplary embodiment. As shown in FIG. 11, in the inactive state, the guide wire 150 extends distally beyond the distal end 132 of the directional guide member 130 and the tip 200.

FIG. 12 is a plan view of the directional guide member 130 as shown in FIG. 10 in an active state in accordance with an exemplary embodiment. As shown in FIG. 12, in the active state, the guide wire 150 is proximal to the tip 200 and housed within the guide wire lumen 140 of the directional guide member 130.

FIGS. 13A-13C are plan views of the dissecting device 100 having a tip 200 on the distal end 132 of the directional guide wire 130 as shown in FIGS. 9A-12. As shown in FIG. 13A, for example, the subintimal space wiring or guide wire 150 is introduced into the subintimal space 30. In FIG. 13B, the dissecting device 100 is placed on the guide wire 150 and is advanced through the subintimal space 30, and for example, performs an atherectomy. In FIG. 13B, the tip 200 of the dissecting device 100 is the inactive state as shown in FIG. 11. In FIG. 13C, the dissecting device 100 performs a re-entry using atherectomy in which the tip 200 of the dissecting device 100 is the active state as shown in FIG. 12.

FIGS. 14A and 14B is a perspective view and an end view, respectively of a dissecting device 100 having a bellow structure 200 in accordance with an alternative embodiment of the first exemplary embodiment. As shown in FIGS. 14A and 14B, the dissecting device 100 includes the directional guide member 130 having a wire lumen 140 therein configured to receive a guide wire 150. The dissecting device 100 also includes the cutting member 110 and the tubular member 120, which is located on the proximal side of the cutting member. In use, the directional guide member 130 is located on a distal side of the cutting member 110 and the tubular member 120. In accordance with an exemplary embodiment on an upper portion 212 of a distal portion 216 of the tubular member 120, a set or a plurality of bellows 220 are located. The set or plurality of bellows 220 are preferably arranged on the upper portion 212 of the tubular member 120, which allows the tubular member 120 to expand and contract. In accordance with an exemplary embodiment, the series or plurality of bellows 220 extend from the upper portion 212 of the tubular member distally to a lower portion 214 of the tubular member 120, which allows the upper portion 212 to expand and contract toward a proximal end of the dissecting device 200.

FIGS. 15A and 15B are perspective views of the dissecting device 100 with a bellow structure 200 as shown in FIG. 14A-14B under threshold and over threshold, respectively. As shown in FIG. 15A, when under threshold, for example, a predetermined amount of force in which the bellows 220 are fully expanded. As shown in FIG. 15B, when the dissecting device 100 is over threshold, for example, the amount of predetermined force is exceed during atherectomy, the bellows 220 contract, which causes the distal end 132 of the directional guide member 130 to raise upward. In accordance with an exemplary embodiment, the amount of force exerted against the dissecting device 100, for example, can be based on an amount of force exerted against the distal end 132 of the directional guide member 130 and the cutting member 110.

FIG. 15C is a perspective view of the dissecting device 100 with a bellow structure 200 as shown in FIG. 14 with a coil type drive shaft (or coiled drive shaft) 240 in accordance with an exemplary embodiment. As shown in FIG. 15C, instead of bellows 220 expanding and contracting based on whether the dissecting device 100 and the bellows 220 are under threshold or over threshold, the tubular member 120 can include a coil type drive shaft 240, which can straighten the tubular member 120, for example, by rotating the drive shaft 240 in a clockwise direction, or alternatively, shorten the tubular structure 120, for example, by rotating the drive shaft 240 in a counterclockwise direction. In accordance with an exemplary embodiment, by rotating the drive shaft 240 in a clockwise or counterclockwise direction, the amount of expansion or contraction of the bellow structure 200 can be controlled without regards to the amount of force exerted against the distal end 132 of the directional guide member 130 and the cutting member 110.

Figure 16H:
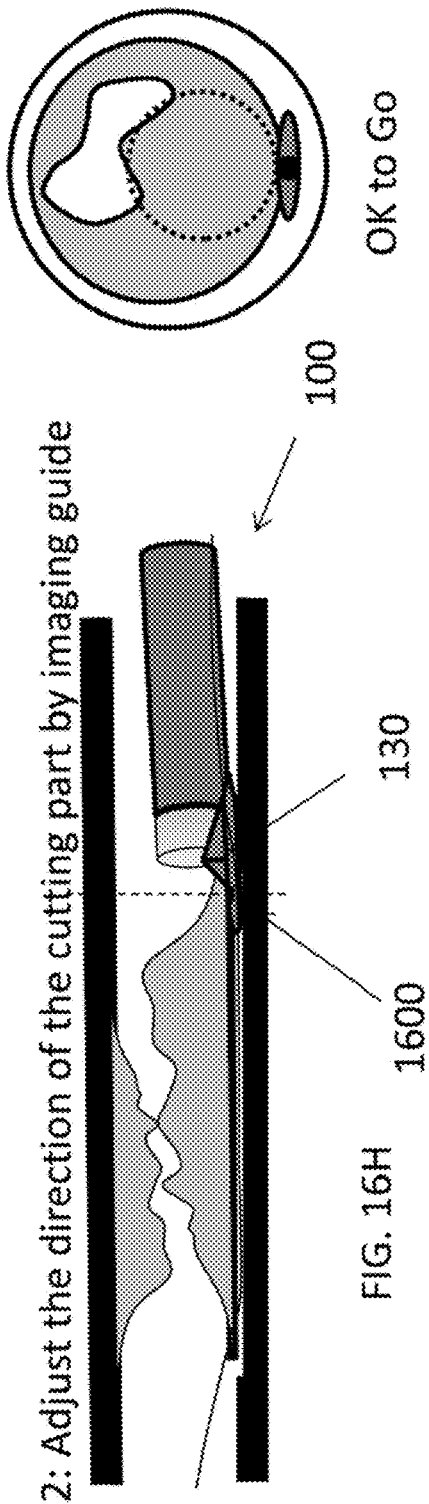
FIGS. 16H and 16I are plan views and views on an imaging device of the dissecting device of FIGS. 16A-16C in accordance with an example (FIG. 16H) in which a direction of the cutting member is good to go, and an example (FIG. 16I, in which the direction of the cutting member is not good to go.

FIGS. 16A-16C are a perspective view, an end view, and a top view, respectively, of the dissecting device 100, which includes the cutting member 110, the directional guide member 130, and an imaging guide 1600 for atherectomy in accordance with an exemplary embodiment. As shown in FIGS. 16A-16C, the imaging guide 1600 can be an imaging portion or an image sensor 1600 located within the directional guide member 130. In accordance with an exemplary embodiment, for example, the imaging guide 1600 can be located between the distal end of the directional guide member 130 and the distal end of the cutting member 120. In accordance with an exemplary embodiment, the directional guiding structure 130 (for example, the tip of the guide member 130, or alternatively, the cutting part of the guiding member 130) can include the imaging portion 1600, which can help the physician, such that the cutting member 120 is not deployed toward the inner surface of the vessel. In other words, the imaging portion 1600 can help the physician deploy the guiding member 130 toward the false lumen of the vessel.

Figure 16I:
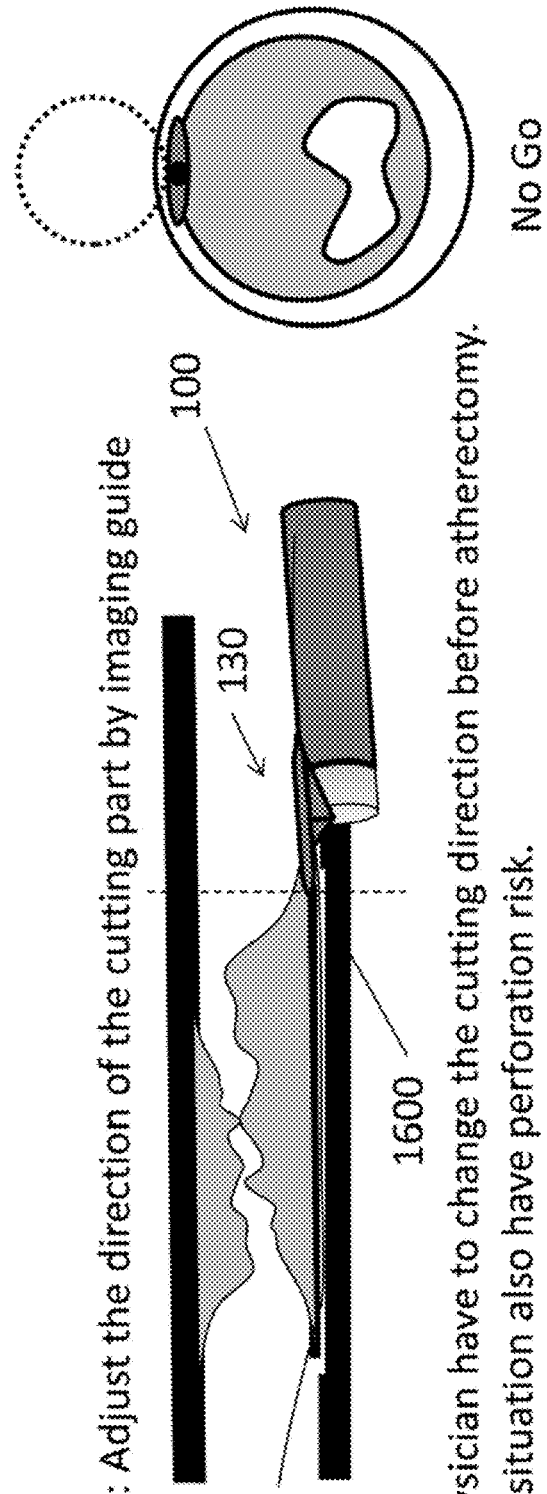

In accordance with an exemplary embodiment as shown in FIG. 16D, the imaging sensor 1600 can allow the physician to observe the direction of the dissecting device 100 on the imaging device, for example, an OCT/IVUS, before the atherectomy procedure. In accordance with an exemplary embodiment, for example, if the direction of the cutting member 110 of the dissecting device 100 is opposite to the stenotic site, for example, as shown in FIG. 16I, the physician can change the direction of the cutting member 110 to the correct side. In addition, the imaging sensor (or imaging guide) 1600 can help reduce perforation risk and improve its debulking efficiency of the dissecting device 100.

Figure 17:
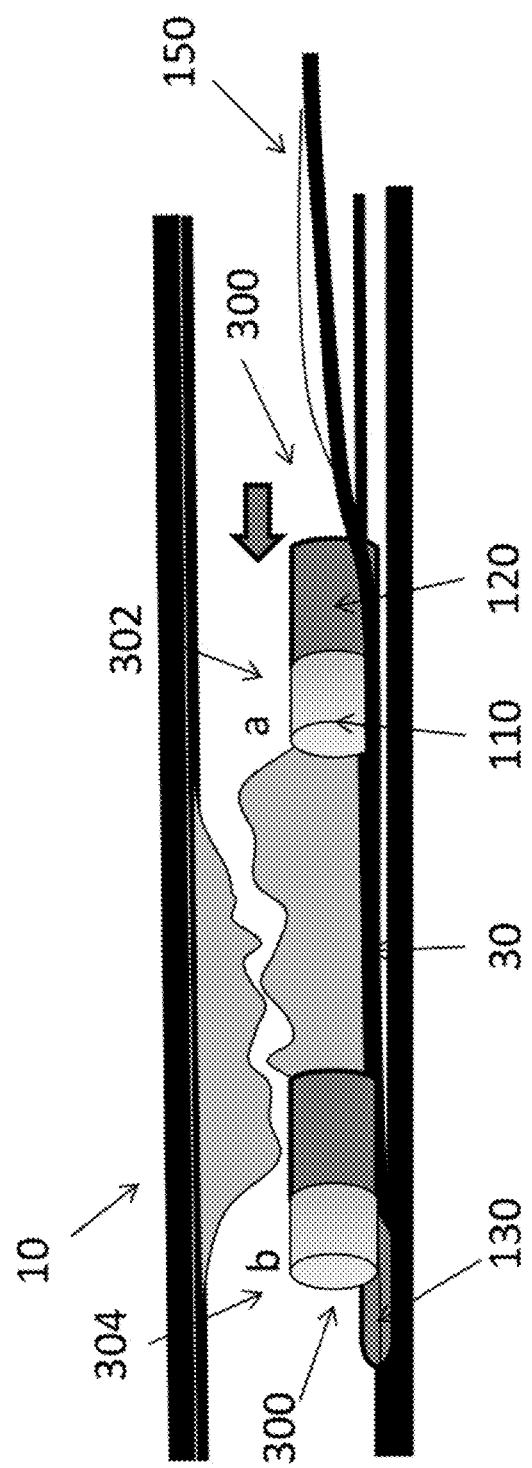
FIG. 17 is a perspective view illustrating a dissecting device having a directional guide member in the subintimal space and a cutting member and tubular member which slide on the directional guide member in accordance with a second exemplary embodiment.

FIG. 17 is a perspective view illustrating a dissecting device 300 comprising a directional guide member 330 in the subintimal space and a cutting member 310 and tubular member 320 which slide on the directional guide member 330 in accordance with a second exemplary embodiment. Note that, in the dissecting member 300 according to the second embodiment, elements having functions and effects the same as or similar to those of the dissecting member 100 according to the first embodiment, are denoted with the same reference signs, and the duplicate descriptions thereof will be omitted. As shown in FIG. 17, rather than the directional guide member 130, the cutting member 110, and the tubular member 120 moving as a single unit on the guide wire 150 in the second exemplary embodiment, the cutting member 310 and the tubular member 320 slide on the directional guide member 330, for example, in the subintimal space 30 from a position "a" 302 to a position "b" 304 located on the distal end of the directional guide member 130.

FIG. 18 is a perspective view of the dissecting device 300 as shown in FIG. 17 in accordance with an exemplary embodiment. As shown in FIG. 18, the dissecting device 300 includes the directional guide member 330, and a cutting member 310 and a tubular member 320 which are slidable on the directional guide member 330. In accordance with an exemplary embodiment, the directional guide member 330 includes a guide wire lumen 340 on at least a distal portion of the directional guide member 330.

FIG. 19 is an end view of the dissecting device 300 as shown in FIG. 18 in accordance with an exemplary embodiment. As shown in FIG. 18, the cutting edge 312 of the cutting member 310 has a generally oval or round shape thereto. In accordance with an exemplary embodiment, the directional guide member 330 can have a rounded distal end with a guide wire lumen 340 located therein. In accordance with an exemplary embodiment, the directional guide member 330 can have a rounded outer diameter, which generally is narrowed at the distal end 332 of the guide member 330 and expands outward moving in a proximal direction towards the cutting member 310.

FIG. 20 is a top view of the dissecting device 300 as shown in FIGS. 18 and 19 in accordance with an exemplary embodiment. As shown in FIG. 20, the directional guide member 330 extends from a distal end 314 of the cutting member 310. In accordance with an exemplary embodiment, the width of the directional guide member 330 can be generally constant with a rounded or oval distal end 332. In addition, the directional guide member 330 has a guide track (or groove) 350 configured to receive a guide member 374 (FIG. 23C) extending from a lower edge or surface of the cutting member 310.

Figure 21A:
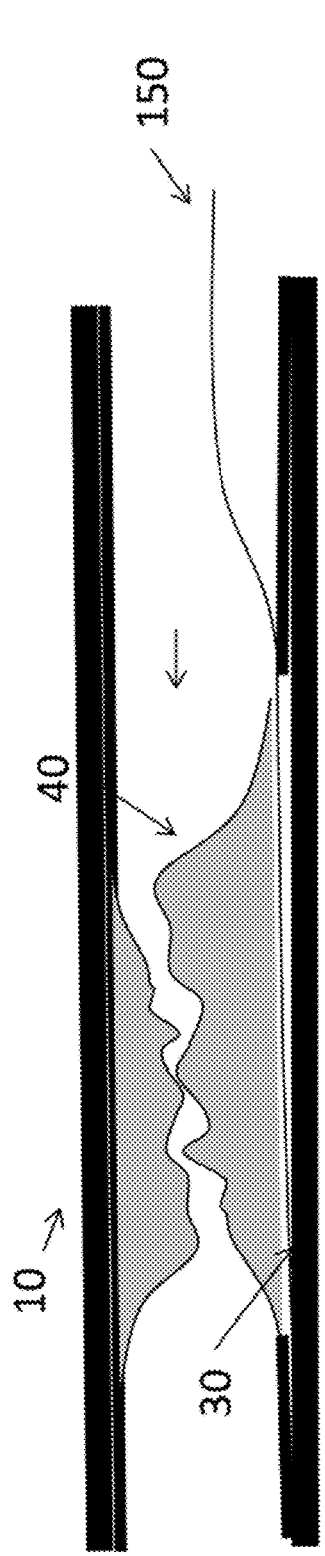
FIGS. 21A-21C are a series of views illustrating the dissecting device as shown in FIGS. 18-20 in use in accordance with an exemplary embodiment.
Figure 21B:
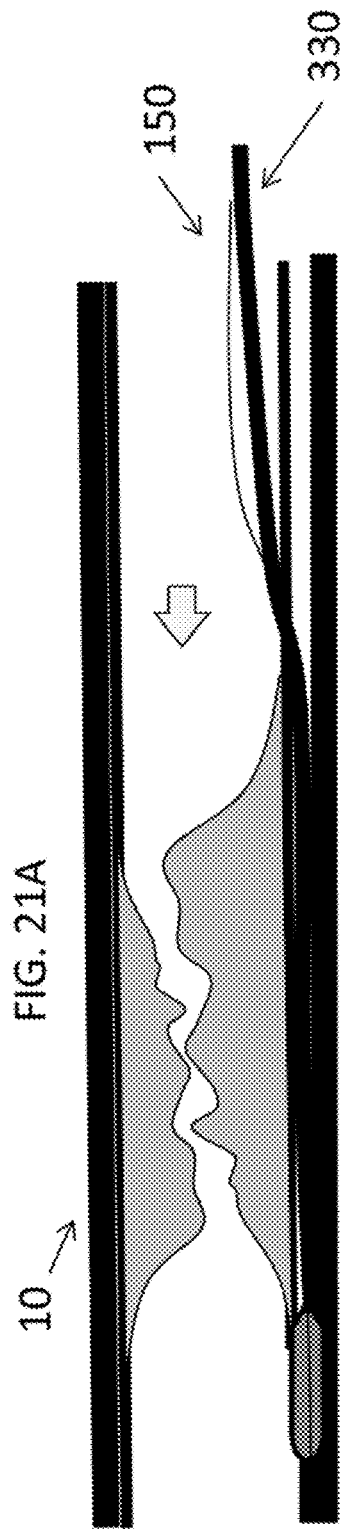
Figure 21C:
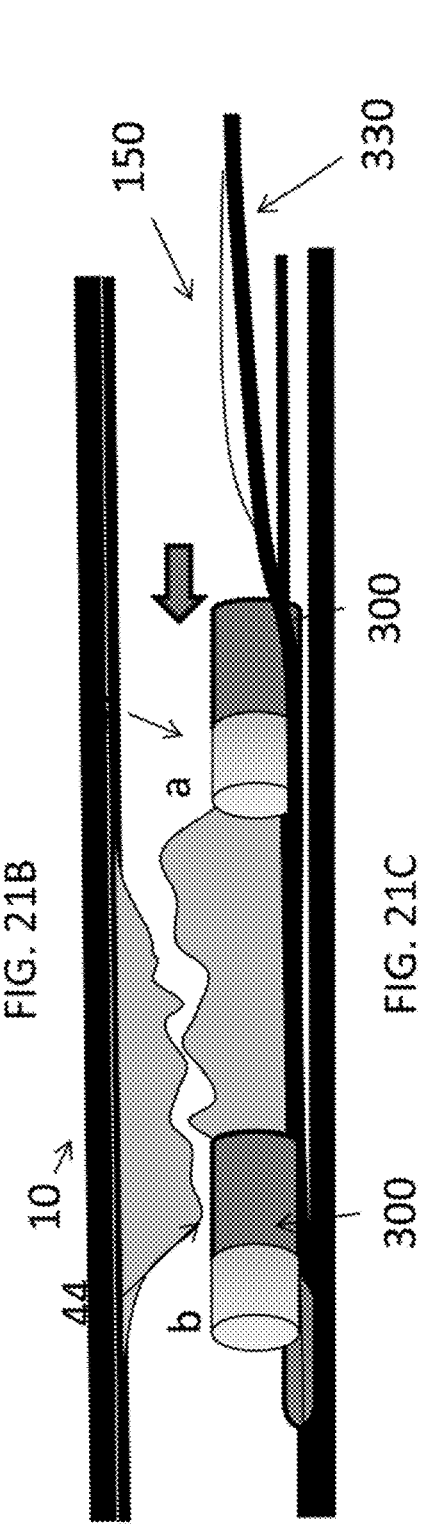

FIGS. 21A-21C are a series of views illustrating the dissecting device 300 as shown in FIGS. 18-20 in use in accordance with an exemplary embodiment. As shown in FIG. 21A, the guide wire 150 is inserted into the blood vessel 10 and through the subintimal space 30 (step 1). As show in FIG. 21B, the directional guide member 330 is then placed onto the guide wire 150 and advance into the blood vessel 10 to a distal end side of the stenosis 40 (step 2). In FIG. 21C, the cutting member 310 and tubular member 320 are placed within a guide track (or groove) 350 on the directional guide member 330 and advanced to the stenosis 40 and cuts or removes the stenosis 40 beginning on the proximal end 42 (position a) of the stenosis 40 through the distal end 44 (position b).

FIG. 22A is a perspective view illustrating the directional guide member 330 of the dissecting device 300 in accordance with an exemplary embodiment. As shown in FIG. 22A, the directional guide member 330 includes a guide track or groove 350, which is configured to receive a guide member 374 (FIG. 23C) on a lower edge of the cutting member 310. The guide track 350 includes a receiving slot 352 and a guide track 354. The receiving track 352 is configured to allow the corresponding guide member 374 on the lower edge of the cutting member 310 to slide along the guide track 354 from entry into the blood vessel 10 through cutting of the stenosis 40. In accordance with an exemplary embodiment, a width of the receiving track 352 is less than a width of the guide track 354 such that once the corresponding guide member 374 is placed within the guide track 350.

FIG. 22B is a perspective view illustrating a cutting member 310 and a tubular member 320 having a bellow structure 220 in accordance with an exemplary embodiment. As shown in FIG. 22B, in accordance with an exemplary embodiment, on an upper portion 212 of a distal portion 216 of the tubular member 320, a set or series of bellows 220 are located. The bellows 220 are arranged on the upper portion 312 of the tubular member 320, which allows the tubular member 320 to expand and contract. In accordance with an exemplary embodiment, the series of bellows 220 extend from the upper portion 312 of the tubular member distally to a lower portion 314 of the tubular member 320, which allows the upper portion 312 to expand and contract in a proximal direction.

FIG. 22C shows perspective views of the cutting member 310 and the tubular member 320 with a bellow structure 220 sliding along the guide member 330. As shown in FIG. 22C, once the cutting member 310 and the tubular member 320 reach a distal end of the guide track 350, a distal end of the cutting member 310 raises upward as the bellows 220 contract. As shown in FIG. 22C, a distal portion 336 of the guide member 330 includes a guide wire lumen 340. In accordance with an exemplary embodiment, the guide wire lumen 340 can rise slightly upward from a proximal side to a distal side of the distal portion 336 of the guide member 330.

FIG. 22D is a top view of the guide member 330 of the dissecting device 300 as shown in FIGS. 22A-22C in accordance with the second exemplary embodiment. As shown in FIG. 22D, the directional guide member 330 includes the guide track or groove 350, which is configured to receive the guide member 374 (FIG. 23C) on a lower edge of the cutting member 310. The guide track 350 extends from a proximal end 334 of the guide member 330 towards the distal end 332 of the guide member 330. On a distal portion 336 of the guide member 330, the guide track 350 ends such that the cutting member 310 and tubular member 320 can to stop and can be contained within the guide track 350 during use. In addition, the guide member 330 includes a guide wire lumen 340, which is located on a distal side of the end of the guide track 350 within the distal portion 336 of the guide member 330. As shown in FIG. 22A, the receiving track 352 is configured to allow the corresponding guide member 374 on the lower edge of the cutting member 310 to slide along the guide track 354 from entry into the blood vessel 10 through cutting of the stenosis 40.

Figure 23C:
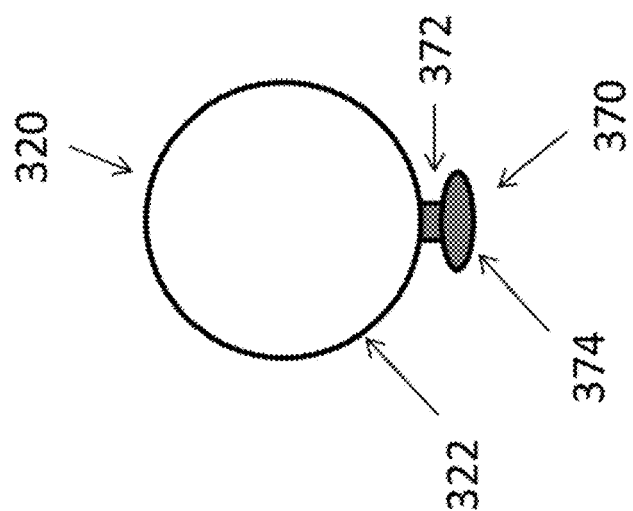
FIG. 23C is a cross-section view along the line XXIIIC-XXIIIC as shown in FIG. 22B of the tubular member in accordance with an exemplary embodiment.
Figure 23B:
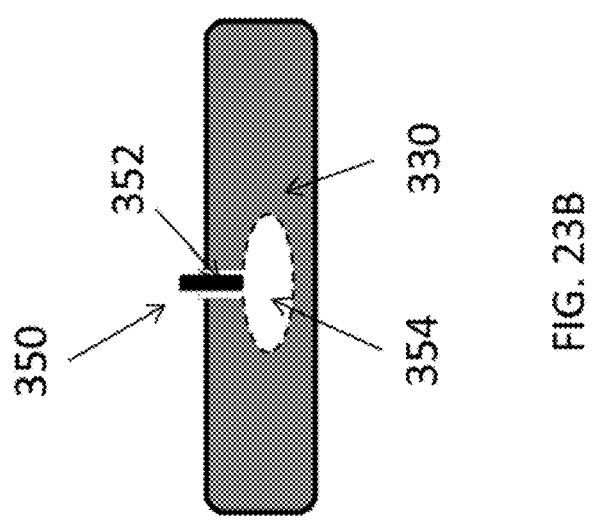
FIG. 23B is a cross-sectional view of the guide member along the line XXIIIB-XXIIIB as shown in FIGS. 22A and 22D in accordance with the first exemplary embodiment.
Figure 23A:
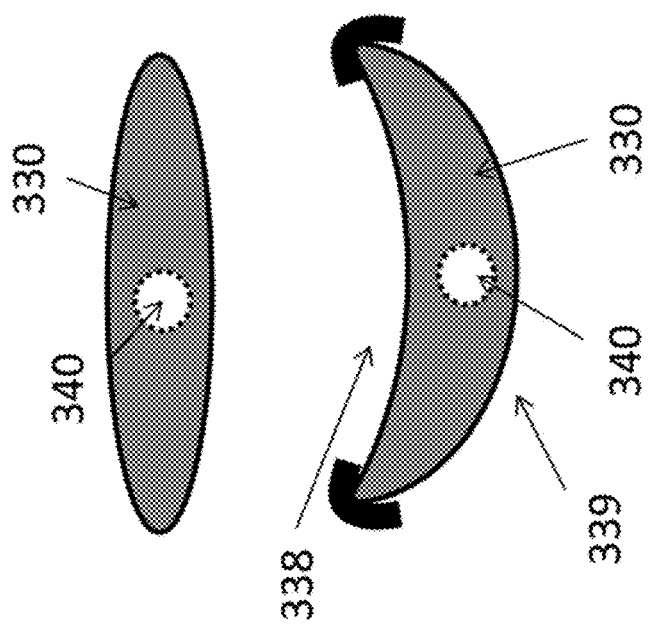
FIG. 23A is a cross-sectional view of the guide member along the line XXIIIA-XXIIIA as shown in FIGS. 22A and 22D in accordance with two exemplary embodiments of the dissecting device in accordance with the first exemplary embodiment.

FIG. 23A is a cross-sectional view of the guide member along the line XXIIIA-XXIIIA as shown in FIGS. 22A and 22D in accordance with two exemplary embodiments of the dissecting device in accordance with the first exemplary embodiment. As shown in FIG. 23A, the distal side of the distal portion of the guide member 330 can have a generally oval shape having a guide wire lumen 340, or alternatively, for example, can be a crescent moon shape having a generally rounded (or convex) outer edge on a lower surface 339 thereof and a concave edge on an upper surface 338 thereof. For example, in accordance with an exemplary embodiment, the lower surface 339 of the guide member 330 can have a shaped, which matches an inner wall of the subintimal (or intima) 30.

FIG. 23B is a cross-sectional view of the guide member along the line XXIIIB-XXIIIB as shown in FIGS. 22A and 22D in accordance with the first exemplary embodiment. In accordance with an exemplary embodiment, as shown in FIG. 23B, the portion of the guide member 330, which houses the guide track 350, can have a generally rectangular outer shape as shown. Alternatively, the guide member 330 in the portion which house the guide track 350 can be oval or crescent moon shaped as shown in FIG. 23A. In accordance with an exemplary embodiment, the portion of the guide member 330, which houses the guide track can have, for example, a shaped, which matches an inner wall of the subintimal (or intima) 30.

FIG. 23C is a cross-section view along the line XXIIIC-XXIIIC as shown in FIG. 22B of the tubular member 320 in accordance with an exemplary embodiment. As shown in FIG. 23C, the tubular member 320 has a generally round or oval outer diameter. On a lower edge 322 of the tubular member 320, an extension member 372 extends from the lower edge 322 of the tubular member 320 to a guide member 374, which is configured to slide within the guide track 350. In accordance with an exemplary embodiment, the guide member 374 is configured to match the guide track 350. For example, in accordance with an exemplary embodiment the guide member 374 has an oval outer diameter, which matches an oval diameter of the guide track 350.

FIG. 24A is a perspective view illustrating the dissecting device 300 with re-entry by a cutting member 310 in accordance with another exemplary embodiment. As shown in FIG. 24A, the directional guide member 330 includes a guide track or groove 350, which is configured to receive a guide member 370 (FIG. 25C) on a lower edge 312 of the cutting member 310, for example, on a proximal side of the tubular cutting member 310, or alternatively, the guide member 370 can be located on the lower edge 322 of the tubular member 320 as shown, for example, in FIGS. 22B and 22C. The guide track 350 includes a receiving slot 352 and a receiving track 354. The receiving slot 352 is configured to allow the corresponding guide member 370 on the lower edge of the cutting member 310 to slide along the receiving track 354 from entry into the blood vessel 10 through cutting of the stenosis 40. In accordance with an exemplary embodiment, a width of the receiving slot 352 is less than a width of the receiving track 354 such that once the corresponding guide member 370 is placed within the guide track 350. In accordance with an exemplary embodiment, the guide member 370 can include a first member 372 extending from a lower surface 312, 322 of the cutting member 310 or the tubular member 320, and a second member 374 configured to slide within the receiving track 354.

FIG. 24B is a perspective view illustrating the dissecting device 300 with re-entry by a cutting member 310 in accordance with an exemplary embodiment. As shown in FIG. 24B, in accordance with an exemplary embodiment, on a lower edge of the cutting member 310, a micro-needle 360 with an elastic material 362 on a proximal side of the micro-needle 360.

FIG. 24C shows perspective views of the dissecting device 300 as the cutting member 310 and tubular member 320 slide along the guide member 330. As shown in FIG. 24C, once the cutting member 310 and the tubular member 320 reach a distal end of the guide track 350, a distal end of the cutting member 310 with the micro-needle 360 raises upward as the cutting member 310 contacts a distal end of the guide track 350. As shown in FIG. 24C, a distal portion 336 of the guide member 330 includes a guide wire lumen 340. In accordance with an exemplary embodiment, the guide wire lumen 340 can rise slightly upward from a proximal side to a distal side of the distal portion 336 of the guide member 330.

FIG. 24D is a top view of the guide member 330 of the dissecting device 300 as shown in FIG. 24A in accordance with the second exemplary embodiment. As shown in FIG. 24D, the guide member 330 includes the guide track or groove 350, which is configured to receive the guide member 374 (FIG. 25C) on a lower edge of the cutting member 310. The guide track 350 extends from a proximal end 334 of the guide member 330 towards the distal end 332 of the guide member 330. On a distal portion 336 of the guide member 330, the guide track 350 ends such that the cutting member 310 and tubular member 320 can to stop and can be contained within the guide track 350 during use. In addition, the guide member 330 includes a guide wire lumen 340, which is located on a distal side of the end of the guide track 350 within the distal portion 336 of the guide member 330. As shown in FIG. 25B, the receiving track 352 and the receiving track 354 are configured to allow the corresponding first member 372 and second member on the lower edge of the cutting member 310 to slide along the guide track 350 from entry into the blood vessel 10 through cutting of the stenosis 40.

Figure 25C:
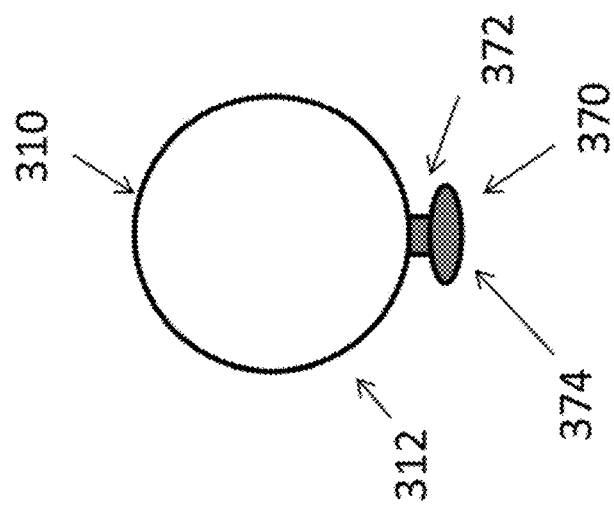
FIG. 25C is a cross-section view along the line XXVC-XXVC as shown in FIG. 24B of the tubular member in accordance with an exemplary embodiment.
Figure 25B:
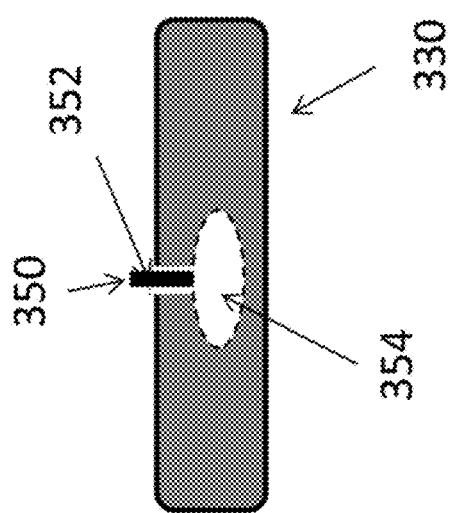
FIG. 25B is a cross-sectional view of the guide member along the line XXVB-XXVB as shown in FIGS. 24A and 24D in accordance with the first exemplary embodiment.
Figure 25A:
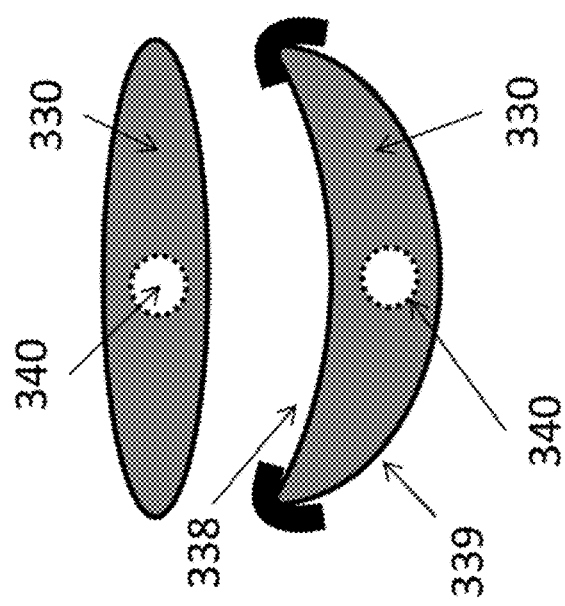
FIG. 25A is a cross-sectional view of the guide member along the line XXVA-XXVA as shown in FIGS. 24A and 24D in accordance with two exemplary embodiments of the dissecting device in accordance with the first exemplary embodiment.

FIG. 25A is a cross-sectional view of the guide member along the line XXVA-XXVA as shown in FIGS. 24A and 24D in accordance with two exemplary embodiments of the dissecting device in accordance with the first exemplary embodiment. As shown in FIG. 25A, the distal side of the distal portion of the guide member 330 can have a generally oval shape having a guide wire lumen 340, or alternatively, for example, can be a crescent moon shape having a generally rounded (or convex) outer edge on a lower surface 339 thereof and a concave edge on an upper surface 338 thereof. For example, in accordance with an exemplary embodiment, the lower surface 339 of the guide member 330 can have a shape, which matches an inner wall of the subintimal (or intima) 30.

FIG. 25B is a cross-sectional view of the guide member along the line XXVB-XXVB as shown in FIGS. 24A and 24D in accordance with the first exemplary embodiment. In accordance with an exemplary embodiment, as shown in FIG. 25B, the portion of the guide member 330, which houses the guide track 350, can have a generally rectangular outer shape as shown. Alternatively, the guide member 330 in the portion which house the guide track 350 can be oval or crescent moon shaped as shown in FIG. 23A. In accordance with an exemplary embodiment, the portion of the guide member 330, which houses the guide track 350 can have, for example, a shape, which matches an inner wall of the subintimal (or intima) 30.

FIG. 25C is a cross-section view along the line XXVC-XXVC as shown in FIG. 24B of the tubular member 320 in accordance with an exemplary embodiment. As shown in FIG. 25C, the tubular member 320 has a generally round or oval outer diameter. On a lower edge 322 of the tubular member 320, an extension member 372 extends from the lower edge 322 of the tubular member 320 to a guide member 374, which is configured to slide within the guide track 350. In accordance with an exemplary embodiment, the guide member 370 is configured to match the guide track 350. For example, in accordance with an exemplary embodiment the second member 374 of the guide member 370 has an oval outer diameter, which matches an oval diameter of the receiving track 354 of the guide track 350. In accordance with an alternative exemplary embodiment, rather than being connected to the tubular cutting member 310, the guide member 370 can be attached to a lower surface of the tubular member 320.

FIG. 26 is a plan view of a dissecting system 400 in accordance with an exemplary embodiment having a cutting member (or first dissecting member) 420 and a second dissecting member 410, and wherein the second dissecting member 410 is shown in a bent state in accordance with a third exemplary embodiment. Note that, according to the third embodiment, elements having functions and effects the same as or similar to those of the dissecting member 100, 300 according to the first and second embodiments, are denoted with the same reference signs, and the duplicate descriptions thereof will be omitted.

As shown in FIG. 26, a guide wire 150 is inserted into the blood vessel 10 and the subintimal space 30. The dissecting system 400 includes the second dissecting member 410 and a cutting device (or first dissecting member) 420, and the dissecting system 400 is guided to the stenosed site 40 by the guide wire 150. As shown in FIG. 26, the second dissecting member 410 in a bent state moves over the whole (or entire) circumference between an inner side 32 of the subintimal space 30 and the outer side 34 of the subintimal space 30 to cut or dissect at least a portion of the stenosed site 40. In accordance with an exemplary embodiment, the second dissecting member 410 can be an elongated wire 412, for example, having an outer diameter of 0.018 to 0.035 inches, for example, 0.018 inches or 0.035 inches made of stainless steel and/or nickel titanium alloy or Nitinol (NiTi), and with or without a hydrophilic polymer coating or Teflon® coating.

FIG. 27 is a cross-sectional view of a blood vessel 10 as shown in FIG. 26 in which the second dissecting member 410 is in a bent state in accordance with the third exemplary embodiment. As shown in FIG. 27, the guide wire 150 is inserted into the subintimal space 30, which guides the dissecting system 400 to the stenosed site 40. In accordance with an exemplary embodiment, the second dissecting member 410 can be positioned between an inner side of the subintimal space and an outer side of the subintimal space. During atherectomy, the second dissecting member 410 dissects the inner side of the subintimal space (stenotic region) over the whole (or entire) circumference and removes the inner side 32 of the subintimal space 30 (and/or stenotic region 40) from the blood vessel 10. In accordance with an exemplary embodiment, by dissecting the stenotic region 40 from the blood vessel 10, a larger lumen 12 can be obtained for improved blood flow.

FIGS. 28A and 28B are plan views of a dissecting member 500, which includes an expandable balloon 510 within a blood vessel 10 in accordance with an exemplary embodiment. As shown in FIG. 28A, the dissecting member 500 includes an expandable balloon 510, which is positioned on a distal portion of a dissecting member 410. In accordance with an exemplary embodiment, the dissecting member 500 is inserted into the blood vessel and through the subintimal space 30 from a proximal side 42 to a distal side 44 of the stenosed site 40 such that the balloon 510 is positioned on a distal side of the stenosed site 40. Once the balloon 510 of the dissecting member 400 is positioned on the distal side of the stenosed site 40, the balloon 510 is expanded to lock or fix the balloon 510 within the blood vessel 10.

In accordance with an exemplary embodiment as shown in FIG. 28B, the dissecting wire 410 is pushed into the blood vessel 10 such that dissecting wire 410 moves in a circumferential direction of the subintimal space 30 in a bent state to remove the inner side 32 of the subintimal space 30 (and/or stenotic region 40) from the blood vessel 10. The dissected inner side 32 of the subintimal space 30 and a stenotic region 40 attached to the inner side 32 of the subintimal space 30 from the blood vessel 10 is then removed.

FIG. 29 is a plan view of a cutting device (or first dissecting device) 420 in accordance with an exemplary embodiment. As shown in FIG. 29, the cutting device 420 can be an elongated member 422 having a lumen 440 extending from a proximal end 426 of the elongated member 422 to the distal end 424 of the elongated member. The lumen 440 can be configured to be place on a guide wire 150 (not shown).

FIG. 30 is a top view of the cutting device 410 of FIG. 29 in accordance with an exemplary embodiment. As shown in FIG. 30, the cutting device 420 includes a cutting blade 430 for distal end incision, and wherein the cutting blade 430 is arranged with a cutout 430 on a distal portion of the cutting device 420.

FIGS. 31A-31C are a series of cross-sectional views of the cutting device 420 of FIG. 30 and cross-sectional view along the lines XXXIA-XXXIA, XXXIB-XXXIB, and XXXIC-XXXIC in accordance with an exemplary embodiment. As shown in FIGS. 31A-31C, the cutting device 420 preferably has an oval shape thereto having a width greater than height configured to be received within a blood vessel 10. A distal end of the cutting device 420 narrows to a rounded distal end 418. The lumen 440 within the cutting device is preferably positioned within a center portion of the cutting device 420. As shown in FIG. 31B, in a distal portion of the cutting device 420, a portion of the elongated member 420 is removed to house the cutting blade 430 for distal end incisions. As shown in FIG. 31C, the cutting device 420 has a generally oval shape having a width greater than a height thereof.

In accordance with an exemplary embodiment, the cutting device 420 can have a width 421 of about 1.0 mm to about 7.0 mm and a thickness (or depth) 423 of about 0.4 mm to about 2.0 mm. In accordance with an exemplary embodiment, the cutting blade 430 located at the tip has a width 425 of about 0.2 mm to 10 mm, and a thickness (or depth) 427 of about 0.5 mm to about 3.0 mm.

Figure 32:
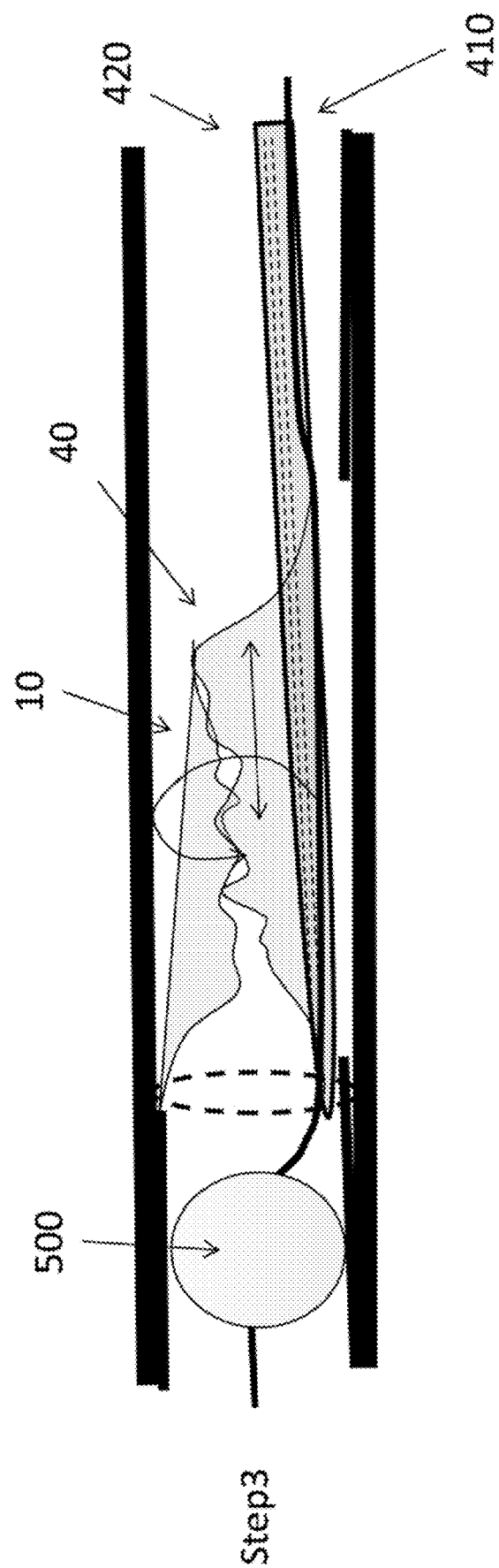
FIG. 32 is a plan view of the dissecting member as a balloon wire as shown in FIG. 29 with a cutting device as shown in FIGS. 30-31C in accordance with an exemplary embodiment.

FIG. 32 is a plan view of the dissecting member 400 as a balloon wire 500 as shown in FIG. 29 with a cutting device 420 as shown in FIGS. 30-31C in accordance with an exemplary embodiment. As shown in FIG. 32, the dissecting member 400 cuts the end of the subintimal space 30 by moving in a circumferential direction or an axial direction of the cutting device 420. In accordance with an exemplary embodiment, in the case of moving in circumferential direction, the cutting device 420 is rotated in the circumferential direction of the subintimal space 30. In the case of the axial direction, the cutting device 420 can be moved distally and proximally repeatedly. For example, in accordance with an exemplary embodiment, the distal and proximal movement at one or more different orientations.

Figure 33:
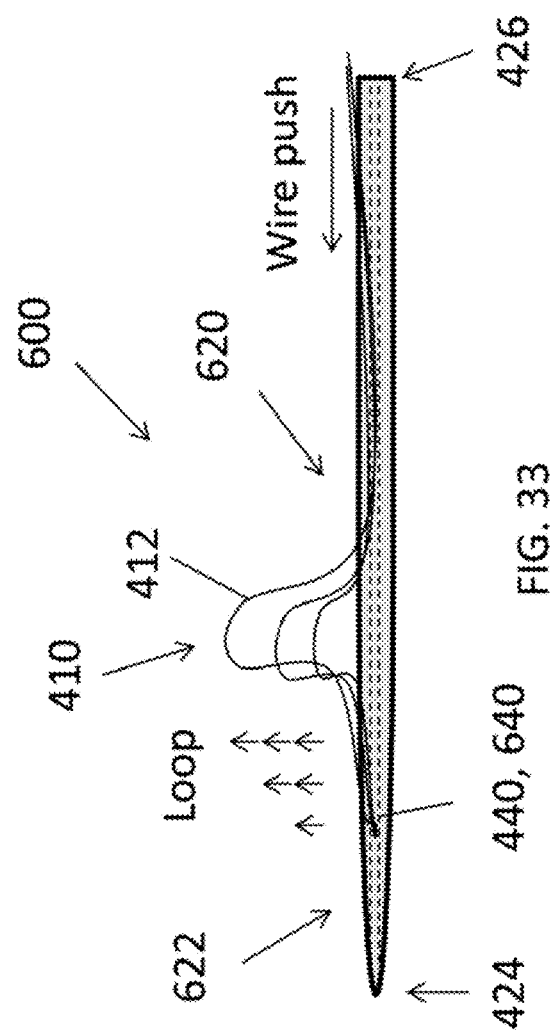
FIG. 33 is a cross-section view of a cutting device having a side port (FIG. 34) for a dissecting member (or second dissecting member) and a cutting blade in accordance with another exemplary embodiment.

FIG. 33 is a cross-section view of a dissecting system 600 having a cutting device (or first dissecting member) 620 having a side port 650 (FIG. 34) for a second dissecting member 410 and an incision portion 630 having a cutting blade 632 in accordance with another exemplary embodiment. As shown in FIG. 33, the cutting member 600 includes a second lumen 640 configured to receive the second dissecting member 410 in the form of a wire 412.

In accordance with an exemplary embodiment, the cutting device 620 can be an elongated member 622 having a first lumen 440 extending from a proximal end 426 of the elongated member 422 to the distal end 424 of the elongated member 622 and configured to receive a guide wire 150, and a second lumen 640 configured to receive a second dissecting member 410 in the form of a dissecting wire 412.

FIG. 34 is a top view of the cutting device 620 of FIG. 33 in accordance with an exemplary embodiment. As shown in FIG. 34, the cutting device 620 includes an incision portion 430 having a cutting blade 432 for distal end incision. In accordance with an exemplary embodiment, the cutting blade 432 can be arranged within the incision portion 430 on a distal portion of the cutting device 420. In addition, the side port 650, which is in communication with the second lumen 640 is configured to receive a dissecting wire 412 (or second dissecting member 410).

As shown in FIG. 34, the first lumen 440 of the cutting device 620 extends to a distal end of the cutting device 600. The second lumen 640 is configured to receive and/or house an end of the second dissecting member 610 before reaching the distal end 424 of the cutting device 620 such that the second dissecting member 410, for example, a wire 412, cannot be pushed though the distal end 424 of the cutting device 620 during use. In accordance with an exemplary embodiment, the second dissecting member 410 in the form of a wire 412 can be fixed within the second lumen 640, or alternatively, may not be fixed in the second lumen 640 and can be removed as needed. The first and second lumens 440, 640 preferably are arranged around a center portion of the elongated cutting device 600.

In accordance with an exemplary embodiment, the second lumen 640 includes a side port 650 located on a proximal side of the cutting member 620. The side port 650 is configured to allow the second dissecting member 410 in the form of a wire 412 to protrude from the second lumen 640 and into the stenosed site 40. In accordance with an exemplary embodiment, the side port 640 is preferably rectangular in shape extending axially for, for example, between 1.5 mm to 0.15 mm.

FIGS. 35A-35D are a series of cross-sectional views of the cutting device 620 of FIG. 34 and cross-sectional view along the lines XXXVA-XXXVA, XXXVB-XXXVB, XXXVC-XXXVC, and XXXVD-XXXVD, respectively, in accordance with an exemplary embodiment. As shown in FIGS. 35A-35D, the cutting device 620 preferably has an oval shape thereto having a width greater than a height thereto, and configured to be received with a blood vessel 10. A distal end 424 of the cutting device 620 narrows to a rounded distal end 418. As shown in FIG. 35C, in a distal portion of the cutting device 420, a portion of the elongated member 420 is removed to house the cutting blade 432 for distal end incisions.

Figure 36:
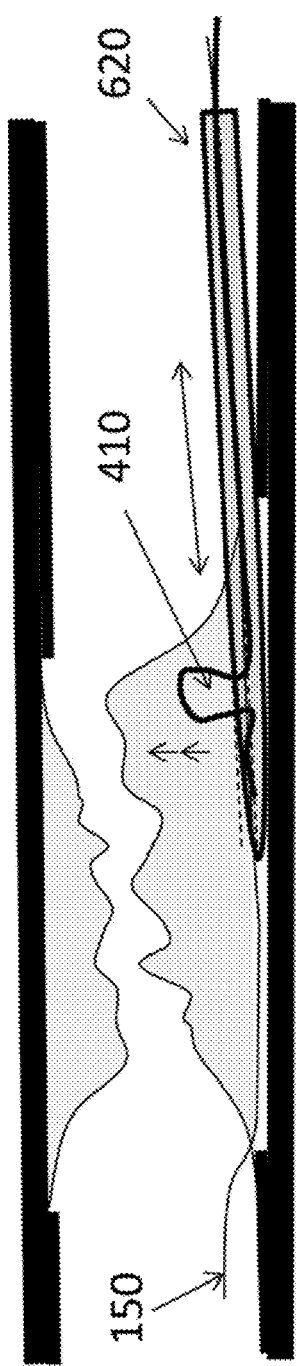
FIG. 36 is a plan view of the dissecting member with a cutting device as shown in FIGS. 33-35D in accordance with an exemplary embodiment.

FIG. 36 is a plan view of the dissecting member 600 with a cutting device 620 as shown in FIGS. 33-35D in accordance with an exemplary embodiment. As shown in FIG. 36, a guide wire 150 is inserted into the subintimal space 30 of the blood vessel 10 at a proximal side of the stenosed region 40 to a distal side of the stenosed site 40. The dissecting member 600 is placed on the guide wire 150 and directed to the stenosed site 40. The first and second dissecting members 620, 410 cut between the inner surface 32 and the outer surface 34 of the subintimal space 30 by moving in a circumferential direction, and/or an axial direction of the cutting device 620.

In accordance with an exemplary embodiment, in the case of moving in circumferential direction, the cutting device 620 is rotated in the circumferential direction of the subintimal space. In the case of the axial direction, the cutting device 620 can be moved distally and proximally repeatedly. As shown in FIG. 36, the second dissecting member 410 in a bent state moves over the whole circumference between an inner side 32 of the subintimal 30 and the outer side 34 of the subintimal 30 to cut or dissect at least a portion of the stenosed site 40. The dissected inner side 32 of the subintimal space 30 and the stenotic region 40 attached to the inner side 32 of the subintimal space 30 are then removed from the blood vessel 10 as disclosed herein. In accordance with an exemplary embodiment, the repeated procedure enables a physician to separate the stenotic region from the vessel wall. For example, afterwards, the physician can remove the cut or dissected portion of the stenosed site by micro forceps, a grasping catheter, snare catheter, aspiration catheter, Fogarty balloon embolectomy, and/or morcellator.

FIG. 37 is a perspective view of a dissecting device 700 having a first dissecting member 710 in the form of a directional guide member 130 and a second dissecting member 720 in the form of a side port 730 configured to receive a wire for a loop wire technique as disclosed herein. The dissecting device 700 includes the directional guide member 130 having a wire lumen 140 therein configured to receive a guide wire 150, and the second dissecting member 720 includes a second lumen (or second dissecting lumen member) 740 (FIG. 38) having a side port 730 (FIG. 39) on an upper surface 732 of the directional guide member 130. As shown in FIG. 37, the dissecting device 700 also includes the cutting member 110 and the tubular member 120, which is located on the proximal side of the cutting member 110. In use, the directional guide member 130 is located on a distal side of the cutting member 110 and the tubular member 120.

FIG. 38 is an end view of the dissecting device 700 as shown in FIG. 37 in accordance with an exemplary embodiment. As shown in FIG. 38, the cutting edge 112 of the cutting member 110 has a generally oval or round shape thereto. In accordance with an exemplary embodiment, the directional guide member 130 can have a rounded distal end with a guide wire lumen 140 and the second lumen 740, which does not extend to a distal end 742 of the directional guide member 130.

FIG. 39 is a top view of the dissecting device 700 as shown in FIGS. 37 and 38 in accordance with an exemplary embodiment. As shown in FIG. 39, the second lumen 740 within the directional guide member 130 has a side port 730 configured to allow a wire 412 to protrude from the second lumen 740 and into the stenosed site 40. In accordance with an exemplary embodiment, the side port 730 is preferably rectangular in shape extending axially for, for example, between 1.5 mm to 15 mm.

Figure 40:
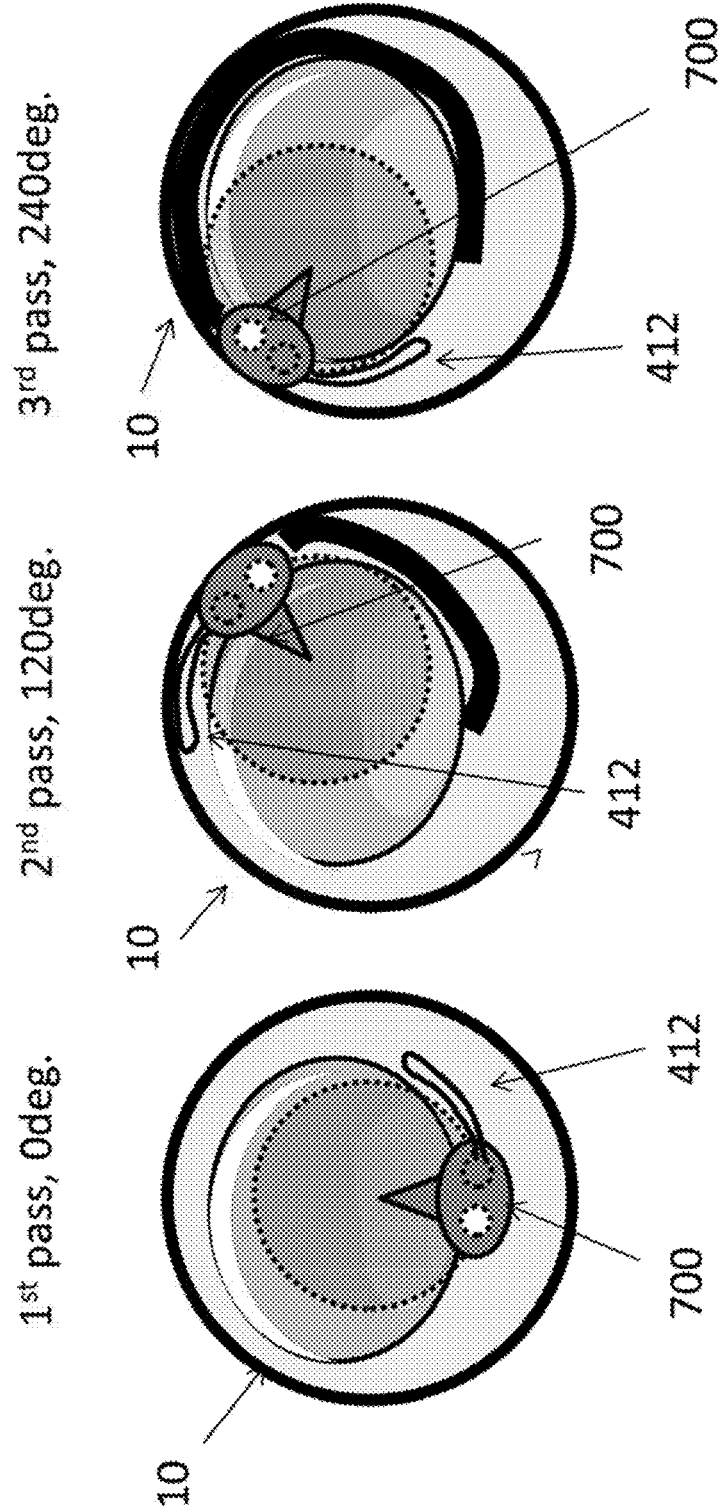
FIG. 40 is a series of cross-sectional view illustrating the use of the dissecting device as shown in FIGS. 37-39 in a blood vessel having a stenosed region.

FIG. 40 is a series of cross-sectional view illustrating the use of the dissecting device as shown in FIGS. 37-39 in a blood vessel 10 having a stenosed region 40. As shown in FIG. 40, the dissecting device 700 can be inserted into the stenosed site 40 in one or more passes, for example, three passes in which during each pass, the directional guide member 130 is rotated in circumferential direction to help assist the wire 412 to separate the subintimal space 30 and the stenosed site 40 from the blood vessel 10. For example, as shown in FIG. 40, for each pass, the directional guide member 130 can be inserted at 120 degrees to the previous pass.

Figure 41:
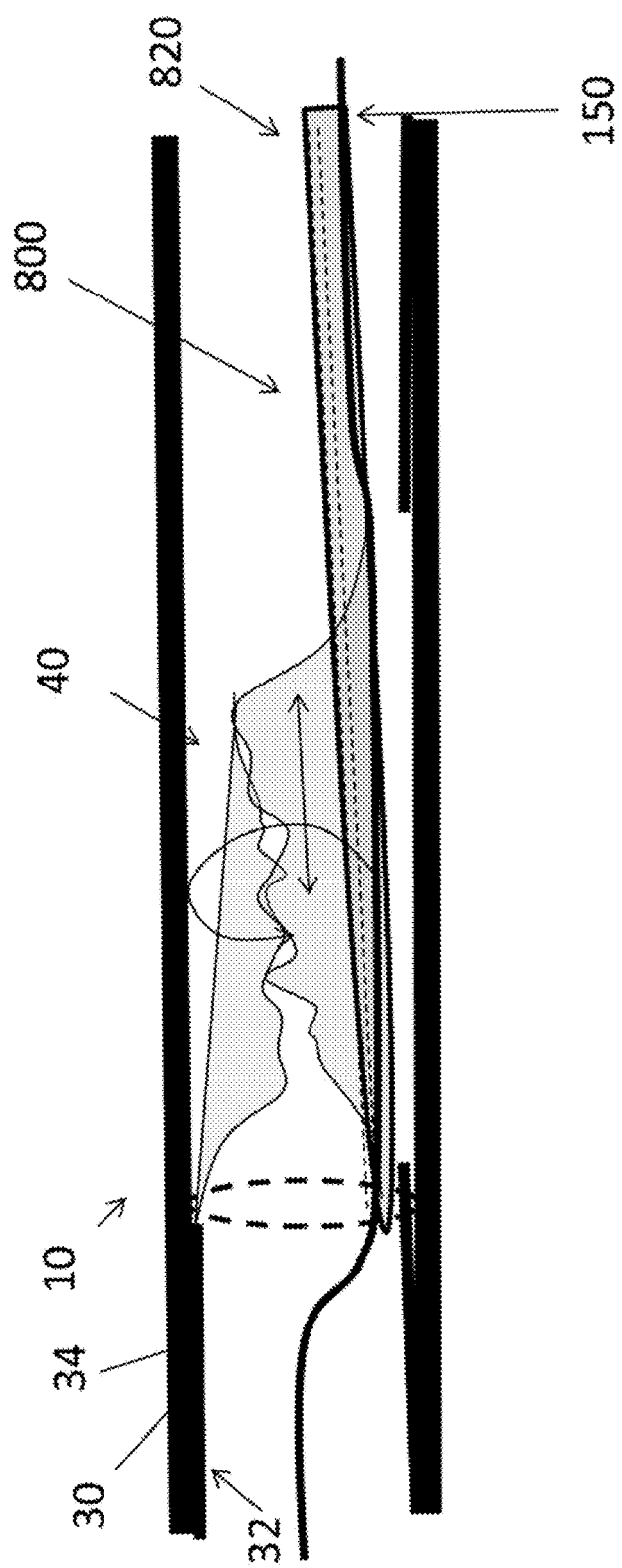
FIG. 41 is a cross-sectional view illustrating the use of the dissecting device in a blood vessel having a stenosed region in accordance with a fourth embodiment.

FIG. 41 is a cross-sectional view illustrating the use of the dissecting device 800 in a blood vessel 10 having a stenosed region 12 in accordance with a fourth embodiment. As shown in FIG. 41, the dissecting device 800 includes an elongated cutting device 820, which rotates over an entire or whole circumference between an inner side or surface 32 of the subintimal space 30 and an outside or outer surface 34 of the subintimal space 30.

FIG. 42 is a perspective view of a cutting device 820 of the dissection device 800 shown in FIG. 41 in accordance with an exemplary embodiment. As shown in FIG. 42, the cutting device 820 can be an elongated member 822 having a lumen 840 extending from a proximal end 826 of the elongated member 822 to the distal end 824 of the elongated member. In accordance with an exemplary embodiment, the lumen 840 can be configured to be placed on a guide wire 150 (FIG. 41).

FIG. 43 is a top view of the cutting device 820 of FIG. 42 in accordance with an exemplary embodiment. As shown in FIG. 43, the cutting device 820 includes an incision portion 830 having a cutting blade 832 for distal end incision. The incision portion 830 is generally arranged on a distal portion of the cutting device 820. In addition, the cutting device 820 can include a convex structure 860 positioned distally to the cutting blade 832, which extends outward from one side of the cutting device 820 and configured to assist the cutting device 820 with removal of the stenosed site 40 from the blood vessel 10.

FIGS. 44A-44D are a series of cross-sectional views of the cutting device 420 of FIG. 43 and cross-sectional view along the lines XLIVA-XLIVA, XLIVB-XLIVB, XLIVC-XLIVC, and XLIVD-XLIVD, respectively, in accordance with an exemplary embodiment. As shown in FIGS. 44A-44D, the cutting device 820 preferably has an oval shape thereto having a width greater than height configured to be received with a blood vessel 10. A distal end of the cutting device 820 narrows to a rounded distal end 818. The lumen 840 within the cutting device 820 is preferably positioned within a center portion of the cutting device 840. As shown in FIG. 44B, in a distal portion of the cutting device 820, a portion of the elongated member 820 is removed to house the cutting blade 832 for distal end incisions. As shown in FIG. 44C, the cutting device 820 include a convex structure 850 on an outer portion of the elongated member 820, which can help remove cut or debulked material from a stenosed site 12.

FIG. 45 is a plan view of the dissecting member 800 as shown in FIGS. 42-44D in accordance with an exemplary embodiment. As shown in FIG. 45, the dissecting member 800 cuts the end of the subintimal space by moving in a circumferential direction or in an axial direction of the cutting device 820. In accordance with an exemplary embodiment, in the case of moving in circumferential direction, the cutting device 820 can be rotated in the circumferential direction of the subintimal space. During rotation of the cutting device 820, the cutting blade 832 cuts or debulks the stenosed region 40, and the convex structure 850 can help removed the cut or debulked material from the stenosed site 12. In the case of the axial direction, the cutting device 820 can be moved before (distally) and after (proximally) repeatedly.

Figure 46:
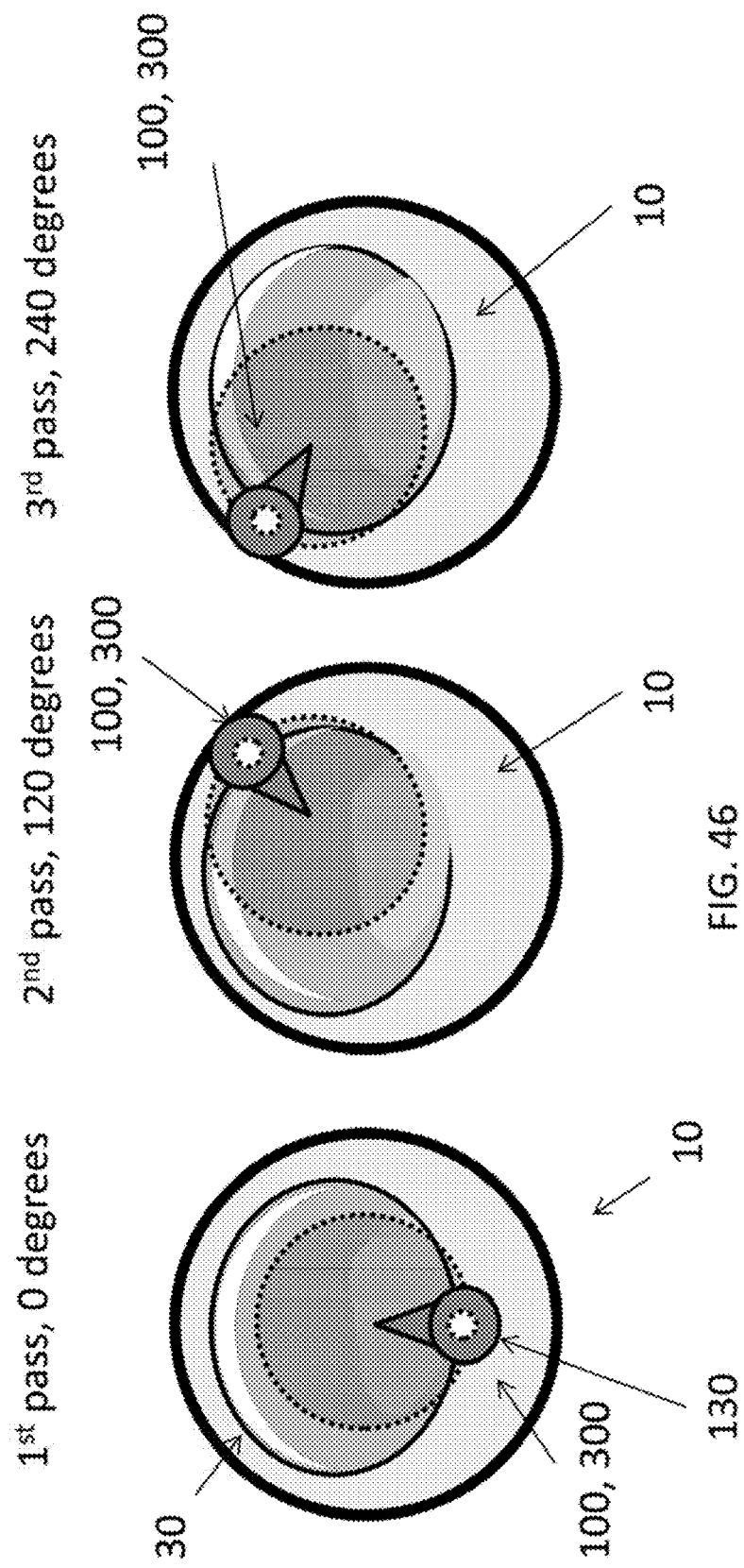
FIG. 46 illustrates a series of end views of an exemplary method of removing a stenosed site from a blood vessel in accordance with an exemplary embodiment.
Figure 47:
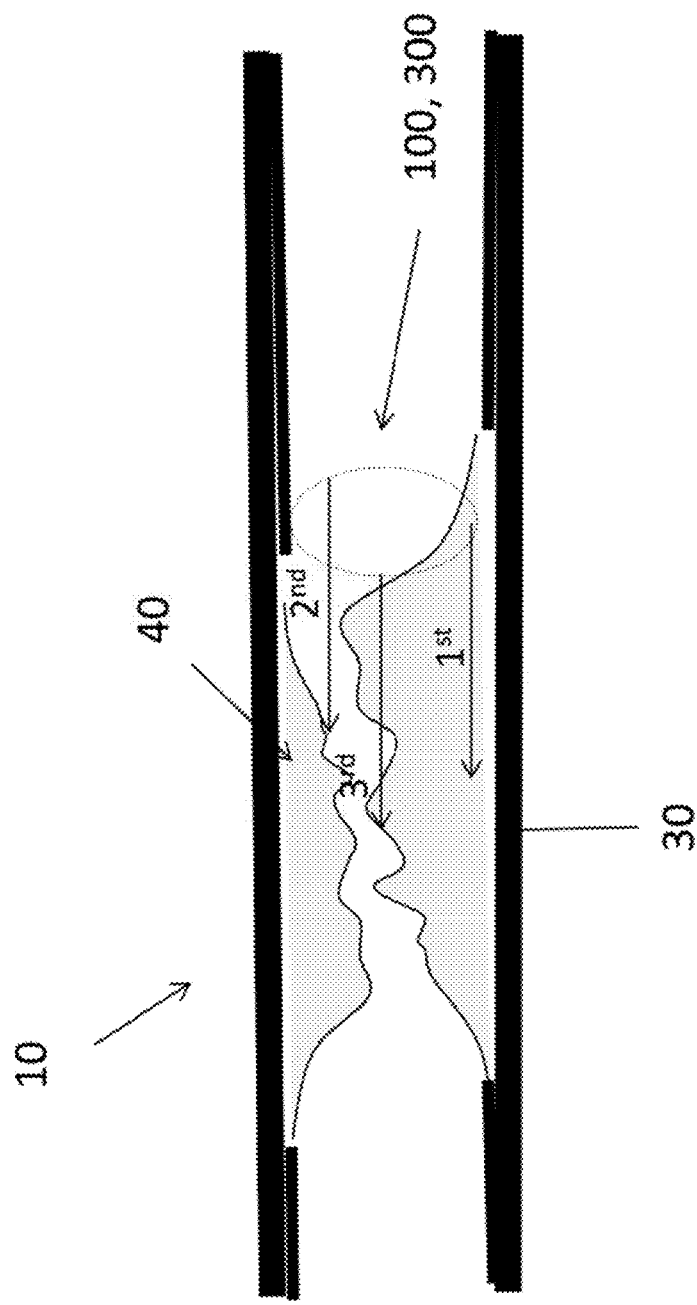
FIG. 47 illustrates a plan view of an exemplary method of removing a stenosed site from a blood vessel in accordance with an exemplary embodiment.

FIGS. 46 and 47 illustrate a series of end views, and a plan view, respectively, of exemplary method of removing a stenosed site 40 from a blood vessel 10 in accordance with an exemplary embodiment. As shown in FIGS. 46 and 47, the dissecting devices 100, 300 as shown in FIGS. 2A-2C, FIGS. 5A-5C, FIGS. 6A-6C, FIGS. 7A-7C, FIGS. 8A-8C, FIGS. 9A-9B, FIGS. 10-12, FIGS. 14A-14B, FIGS. 18-20, FIGS. 22A-23C, FIGS. 24A-25C, can be used by performing repeated atherectomy or a series of passes into and through the stenosed region 40. For example, a first pass can be performed with the directional guide member 130 at a first position, for example, at 0 degrees, a second pass wherein the directional guide member 130 has been rotated 120 degrees from the first atherectomy, and a third pass, where the directional guide member 130 has been rotated 240 degrees from the first atherectomy.

Figure 48:
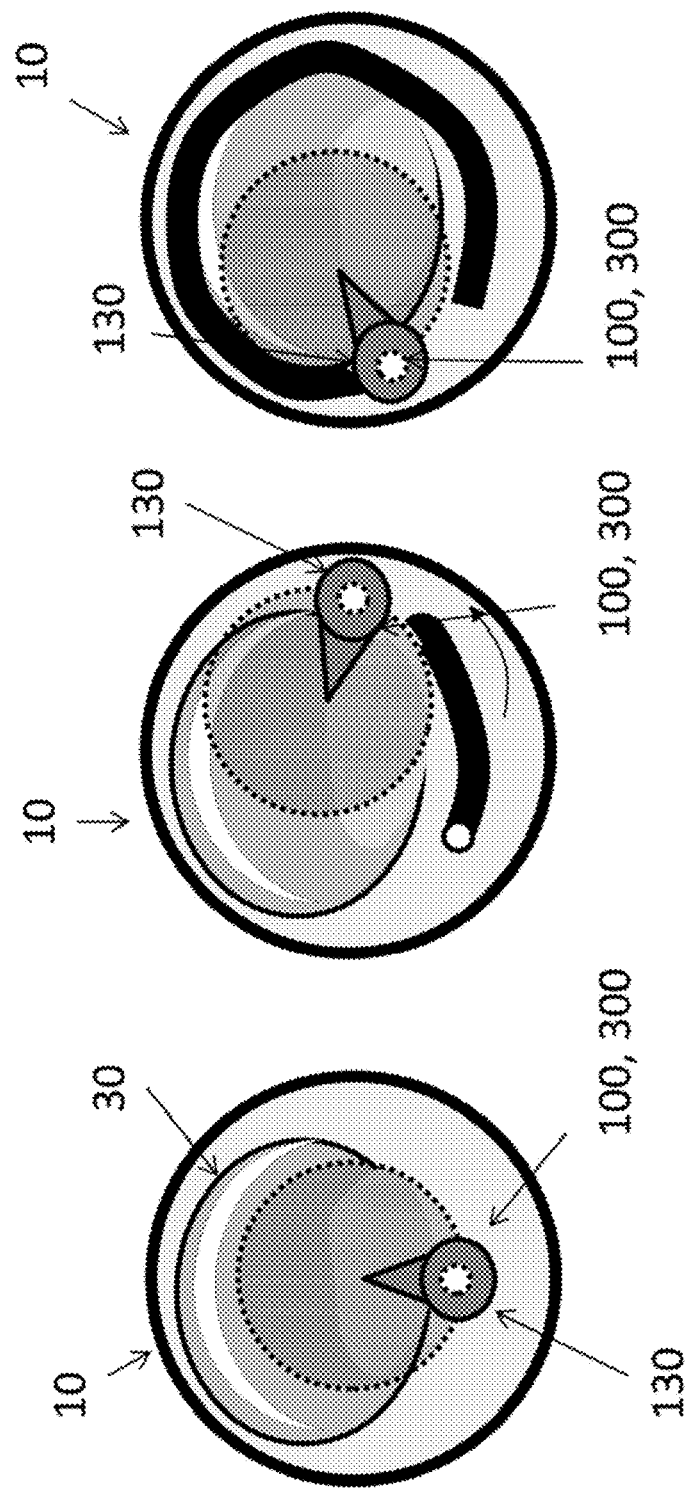
FIG. 48 illustrates a series of end views of another exemplary method of removing a stenosed site from a blood vessel in accordance with an exemplary embodiment.
Figure 49:
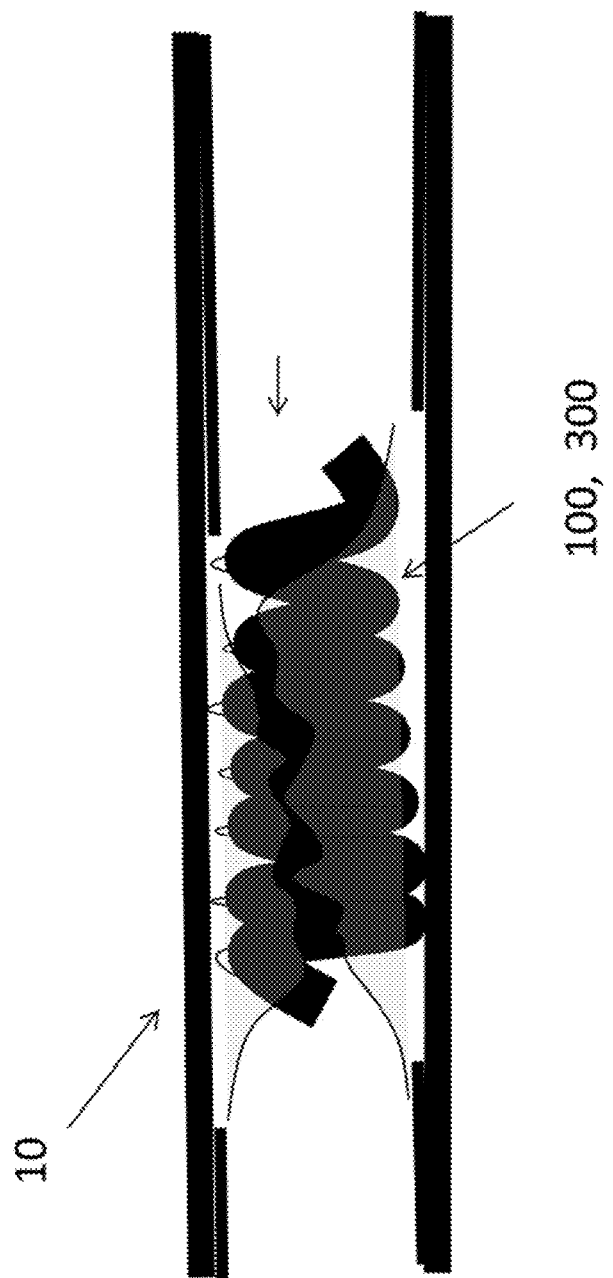
FIG. 49 illustrates a plan view of an exemplary method of removing a stenosed site from a blood vessel in accordance with an exemplary embodiment.

FIGS. 48 and 49 illustrate a series of end views, and a plan view, respectively, of another exemplary method of removing a stenosed site 40 from a blood vessel 10. As shown in FIGS. 48 and 49, the dissecting devices 100, 300 as shown in FIGS. 2A-2C, FIGS. 5A-5C, FIGS. 6A-6C, FIGS. 7A-7C, FIGS. 8A-8C, FIGS. 9A-9B, FIGS. 10-12, FIGS. 14A-14B, FIGS. 18-20, FIGS. 22A-23C, FIGS. 24A-25C as disclosed herein, can be used by performing atherectomy by a rotation or a spiral motion of the dissecting device 100, 300 into and through the stenosed region 40. For example, in accordance with an exemplary embodiment, the dissecting devices 100, 300 as disclosed herein can be moved or pushed distally into the stenosed region 40 at the same time the dissecting device 100, 300 is rotated in a clockwise or counterclockwise direction, which can help enable the device 100, 300 to separate the subintimal 30 from the media 20 around an entirety or whole circumference of the blood vessel 10.

FIG. 50 is a perspective view of a dissecting device 1000 in accordance with an alternative embodiment. As shown in FIG. 50, the dissecting device 1000 can include a directional guide member 130 having a wire lumen 140 therein configured to receive a guide wire 150. The dissecting device 100 can also include a second dissecting member 1010, which extends from a second tubular member 1020. In accordance with an exemplary embodiment, the second tubular member 1020 is arranged around an outer surface 121 of the tubular member 120. In use, the directional guide member 130 is located on a distal side of the tubular member 120. In accordance with an exemplary embodiment, the tubular member 120 can include an optional cutting member (not shown) arranged on a distal end of the tubular member 120.

FIG. 51 is an end view of the dissecting device as shown in FIG. 50 in accordance with an exemplary embodiment. As shown in FIG. 50, the tubular member 120 has a generally oval or round shape thereto. In accordance with an exemplary embodiment, the directional guide member 130 can have a rounded distal end with a guide wire lumen 140 as disclose herein. In accordance with an exemplary embodiment, the directional guide member 130 can have a rounded outer diameter, which can be narrowed at the distal end of the guide member 130 and expands outward moving a proximal direction towards the cutting member 110.

As shown in FIG. 51, the second dissecting member 1010 can be arranged and configured to extend distally from the second tubular member 1020. The second dissecting member 1010 preferably includes a cutting member or blade 1012 on an axially extending rod or member 1014. In accordance with an exemplary embodiment, the second tubular member 1020 is configured to rotate around the tubular member 120 such that the cutting member or blade 1012 on the axially extending rod 1014 can move proximally and distally relative to the directional guide member 130 in addition to rotating around the tubular member 120.

FIG. 52 is series of end views showing the dissecting device 1000 as shown in FIGS. 50 and 51 in a blood vessel 10 having a stenosed region 40. As shown in FIG. 52, the dissecting device 1000 can perform an atherectomy by rotation or a spiral motion of the dissecting device 1000 into and through the stenosed region 40.

FIG. 53 is a perspective view of the dissecting device 1100 in accordance with the first exemplary embodiment. As shown in FIG. 53, the dissecting device includes a directional guide member 130 having a wire lumen 140 therein configured to receive a guide wire 150. The dissecting device 100 includes the cutting member 110 and the tubular member 120, which is located on the proximal side of the cutting member 110. In use, the directional guide member 130 is located on a distal side of the cutting member 110 and the tubular member 120. As shown in FIG. 53, a side-cutting member or blade 1110 is arranged on an outer diameter 111 of the cutting member 110. The side-cutting member or blade 1110 includes a blade or tip 1112, which configured to cut in at least one direction, for example, a clockwise or a counterclockwise direction. In accordance with an exemplary embodiment, the side-cutting member or blade 1110 can be configured that the blade or tip 1112 cuts in both a clockwise and a counter clockwise direction.

FIG. 54 is an end view of the dissecting device 1100 as shown in FIG. 53 in accordance with an exemplary embodiment. As shown in FIG. 54, a cutting edge 112 of the cutting member 110 has a generally oval or round shape thereto. In accordance with an exemplary embodiment, the directional guide member 130 can have a rounded distal end with a guide wire lumen 140. In accordance with an exemplary embodiment, the directional guide member 130 can have a rounded outer diameter, which generally is narrowed at the distal end of the guide member 130 and expands outward moving a proximal direction towards the cutting member 110.

FIG. 55 is series of end views showing the dissecting device 1100 as shown in FIGS. 53 and 54 in a blood vessel having a stenosed region 40. As shown in FIG. 55, the dissecting device 1100 as disclosed herein can perform an atherectomy by rotation or a spiral motion of the dissecting device 1100 into and through the stenosed region 40. As shown in FIG. 55, the dissecting device 1100 can be rotated about an entire circumference of the blood vessel (for example, 360 degrees) to separate the subintimal 30 from the media 20.

Figure 56:
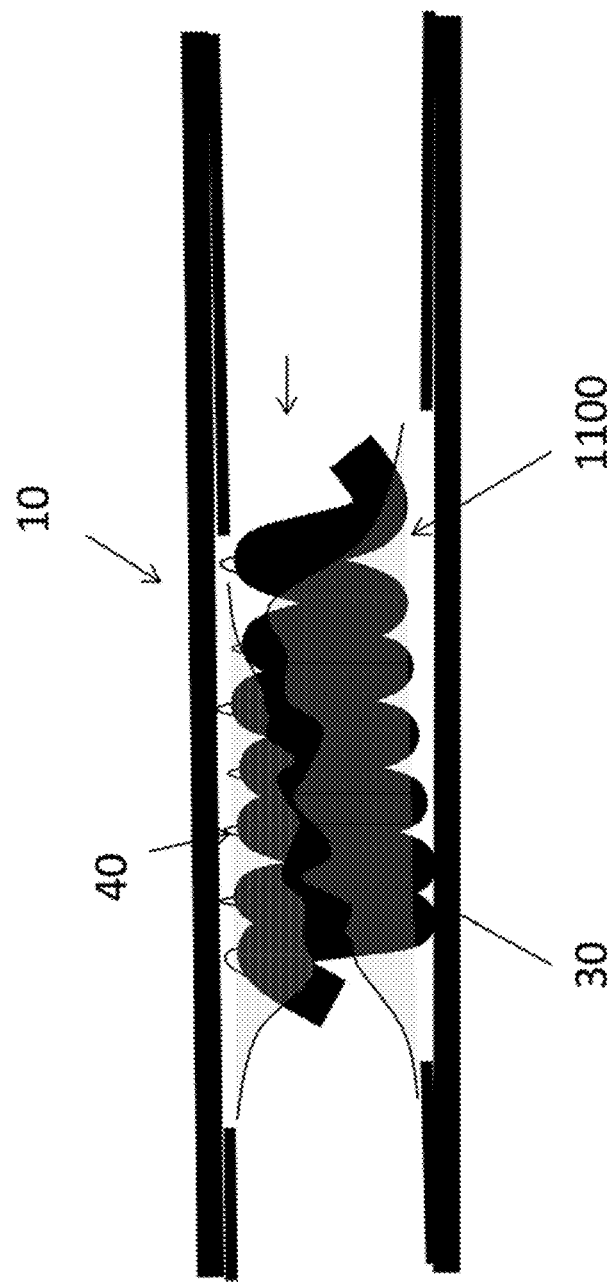
FIG. 56 is a plan view of the dissecting member as shown in FIGS. 53 and 54 in accordance with an exemplary embodiment.

FIG. 56 is a plan view of the dissecting member 1100 as shown in FIGS. 53 and 54 in accordance with an exemplary embodiment. As shown in FIG. 56, the dissecting member cuts 1100 the end of the subintimal space by moving in a circumferential direction of the dissecting device 1100. In accordance with an exemplary embodiment, in the case of moving in circumferential direction, the dissecting device 1100 is rotated in the circumferential direction of the subintimal space 30 such that the side cutting member or blade 1110 cuts or separated the subintimal 30 from the media 20 about an entirety (or 360 degrees) of the blood vessel 10.

The detailed description above describes medical device and treatment methods for treating a stenotic vessel with atherectomy with the subintimal space. The invention is not limited, however, to the precise embodiments and variations described. Various changes, modifications and equivalents can effected by one skilled in the art without departing from the spirit and scope of the invention as defined in the accompanying claims. It is expressly intended that all such changes, modifications and equivalents which fall within the scope of the claims are embraced by the claims.

What is claimed is:

1. A method for treating a stenotic vessel, the method comprising:
    inserting a first dissecting member into a subintimal space of a blood vessel and a second dissecting device configured to be received within a lumen within the first dissecting device and inserted into the blood vessel in a bent state;
    dissecting an inner side of the subintimal space from an outer side of the subintimal space over an entire circumference of the blood vessel with the first dissecting device; and
    removing the dissected inner side of the subintimal space and a stenotic region attached to the inner side of the subintimal space from the blood vessel.

2. The method of claim 1, comprising:
    dissecting the inner side of the subintimal space from the outside of the subintimal space over the entire circumference with the first dissecting member, the first dissecting member having a cutting member on a distal end of the first dissecting member; and
    rotating the first dissecting member around the entire circumference of the blood vessel to separate the inner side of the subintimal space and the stenotic region from the outer side of the subintimal space.

3. The method of claim 1, comprising:
    dissecting the inner side of the subintimal space from the outside of the subintimal space over the entire circumference with the first dissecting member, the first dissecting member having a cutting member on a side portion of the first dissecting member; and
    rotating the first dissecting member around the entire circumference of the blood vessel to separate the inner side of the subintimal space and the stenotic region from the outer side of the subintimal space.

4. The method of claim 1, comprising:
    dissecting the inner side of the subintimal space from the outside of the subintimal space over the entire circumference with the first dissecting member, the first dissecting member including an elongated member having a guide wire lumen extending though at least a portion of the elongated member and an incision portion on a side portion of the elongated member on a distal portion of the elongated member, the incision portion having a cutting blade;
    inserting the elongated member into the subintimal space on a proximal end of a stenotic region and through the subintimal space to a distal end of the stenotic region; and
    rotating the first dissecting device around the entire circumference of the blood vessel to separate the inner side of the subintimal space and the stenotic region from the outer side of the subintimal space.

5. The method of claim 1, comprising:
    dissecting the inner side of the subintimal space from the outside of the subintimal space over the entire circumference with the first dissecting member, the first dissecting member including an elongated member having a guide wire lumen extending though at least a portion of the elongated member and a second lumen configured to receive the second dissecting member, the elongated member having a side port in communication with the blood vessel;
    inserting the elongated member into the subintimal space on a proximal side of the stenotic region and through the subintimal space to a distal side of the stenotic region;
    pushing the second dissecting member into the second lumen in an axial direction such that at least a portion of the second dissecting member exits the side portion into the blood vessel in the bent state; and
    rotating the first and second dissecting devices around the entire circumference of the blood vessel to separate the inner side of the subintimal space and the stenotic region from the outer side of the subintimal space.

6. The method of claim 1, comprising:
    dissecting the inner side of the subintimal space from the outside of the subintimal space over the entire circumference with the first dissecting member and the second dissecting member, the first dissecting member including a directional guide member having a first lumen and a second lumen, the first lumen configured to receive a guide wire, the guide wire lumen extending through at least a portion of the directional guide member and exiting on a distal end of the directional guide member, the second lumen configured to receive the second dissecting member and exits to a side port in the directional guide member in a wire loop extension, and a tubular cutting member configured to cut a stenotic region in the subintimal space;

inserting the directional guide member into the subintimal space on a proximal side of the stenotic region at a first orientation and pushing the directional guide member with the first and second dissecting members through the subintimal space to a distal side of the stenotic region;

moving the directional guide member in a proximal direction to the proximal side of the stenotic region;

changing the orientation of the directional guide member by rotating the first and the second dissecting member to at least one second orientation; and inserting the directional guide member into the subintimal space on the proximal side of the stenotic region at the at least one second orientation and pushing the directional guide member with the first and second dissecting members in an axial direction thought the subintimal space to the distal side of the stenotic region.

7. The method of claim 1, comprising:

dissecting the inner side of the subintimal space from the outside of the subintimal space over the entire circumference with the second dissecting member, the second dissecting member including a wire loop extension; and rotating the second dissecting member around the entire circumference of the blood vessel to separate the inner side of the subintimal space and the stenotic region from the outer side of the subintimal space.

8. The method of claim 1, comprising:

dissecting the inner side of the subintimal space from the outside of the subintimal space over the entire circumference with the second dissecting member, the second dissecting member including a wire loop extension; and moving the second dissecting member in an axial direction of the blood vessel to separate the inner side of the subintimal space and the stenotic region from the outer side of the subintimal space.

9. A method for treating a stenotic vessel, the method comprising:

inserting a balloon wire into a subintimal space on a proximal side of a stenotic region and through the subintimal space to a distal side of the stenotic region, the balloon wire including a balloon and a wire;

inflating the balloon of the balloon wire on the distal side of the stenotic region of the blood vessel;

pushing the wire towards the inflated balloon and into the stenotic region; and dissecting an inner side of the subintimal space from an outer side of the subintimal space over an entire circumference of the blood vessel with the wire in a bent state.

10. The method of claim 9, comprising:

removing the dissected inner side of the subintimal space and a stenotic region attached to the inner side of the subintimal space from the blood vessel.

* * * * *